(12) United States Patent
Sem et al.

(10) Patent No.: US 7,653,490 B2
(45) Date of Patent: Jan. 26, 2010

(54) NUCLEAR MAGNETIC RESONANCE ASSEMBLY OF CHEMICAL ENTITIES

(75) Inventors: Daniel S. Sem, San Diego, CA (US); Maurizio Pellecchia, San Diego, CA (US); Qing Dong, San Diego, CA (US); Mark Kelly, San Diego, CA (US); Min S. Lee, Carlsbad, CA (US)

(73) Assignee: Triad Liquidating Company LLC, Rancho Santa Fe, CA (US)

( * ) Notice: Subject to any disclaimer, the term of this patent is extended or adjusted under 35 U.S.C. 154(b) by 203 days.

(21) Appl. No.: 10/172,485

(22) Filed: Jun. 13, 2002

(65) Prior Publication Data

US 2003/0113751 A1 Jun. 19, 2003

Related U.S. Application Data

(60) Provisional application No. 60/340,219, filed on Dec. 13, 2001, provisional application No. 60/322,574, filed on Sep. 10, 2001.

(51) Int. Cl.
*G06F 7/00* (2006.01)
(52) U.S. Cl. ............... 702/19; 702/20; 703/11; 703/13; 707/102; 530/350
(58) Field of Classification Search ............ 702/19; 435/4
See application file for complete search history.

(56) References Cited

U.S. PATENT DOCUMENTS

| | | | |
|---|---|---|---|
| 4,863,876 A | 9/1989 | Hevey | 436/537 |
| 5,422,281 A | 6/1995 | Harris et al. | 436/501 |
| 5,470,753 A | 11/1995 | Sepetov et al. | 436/89 |
| 5,527,686 A | 6/1996 | Fitzpatrick et al. | 435/7.9 |
| 5,585,277 A | 12/1996 | Bowie et al. | 436/518 |
| 5,658,739 A | 8/1997 | Woods, Jr. | 435/7.1 |
| 5,661,019 A | 8/1997 | Oh et al. | 435/174 |
| 5,679,582 A | 10/1997 | Bowie et al. | 436/518 |
| 5,693,515 A | 12/1997 | Clark et al. | 435/184 |
| 5,698,401 A | 12/1997 | Fesik et al. | 435/7.1 |
| 5,710,009 A | 1/1998 | Fitzpatrick et al. | 435/7.9 |
| 5,710,129 A | 1/1998 | Lynch et al. | 514/18 |
| 5,717,092 A | 2/1998 | Armistead et al. | 544/129 |
| 5,723,490 A | 3/1998 | Tung | 514/478 |
| 5,804,390 A | 9/1998 | Fesik et al. | 435/7.1 |
| 5,830,462 A | 11/1998 | Crabtree et al. | 424/93.21 |
| 6,071,515 A | 6/2000 | Mezes et al. | 424/130 |
| 6,214,561 B1 | 4/2001 | Peters et al. | 435/7.1 |
| 6,333,149 B1 | 12/2001 | Sem | 435/4 |

FOREIGN PATENT DOCUMENTS

| | | |
|---|---|---|
| WO | WO 89/04315 | 5/1989 |
| WO | WO 97/18469 | 5/1997 |
| WO | WO 97/18471 | 5/1997 |
| WO | WO 98/48264 | 10/1998 |
| WO | WO 99/60404 | 11/1999 |

OTHER PUBLICATIONS

Sem et al. Journal of Cellular Biochemistry Supplement 37:99-105 (2001).*
Dabora et al., "Structure of the Acid State os *Escherichia coli* Ribonuclease HI," *Biochemistry* 35:11951-11958 (1996).
Holmbeck et al., "High-resolution Solution Structure of the Retinoid X Receptor DNA-binding Domain," *J. Mol. Biol.* 281:271-284 (1998).
Appelt et al., "Design of Enzyme Inhibitors Using Iterative Protein Crystallographic Analysis," *J. Med. Chem.*, 34:1925-1934 (1991).
Baldock et al., "A Mechanism of Drug Action Revealed by Structural Studies of Enoyl Reductase," *Science*, 274:2107-2110 (1996).
Bayomi et al., "Probing The Thymidylate Synthase Active Site With Bisubstrate Analog Inhibitors," *Nucleosides & Nucleotides*, 7:103-115 (1988).
Bellamacina, C., "The nicotinamide dinucleotide binding motif: a comparison of nucleotide binding proteins," *FASEB J.*, 10:1257-1269 (1996).
Bemis and Murcko, "The Properties of Known Drugs. 1. Molecular Frameworks," *J. Med. Chem.*, 39:2887-2893 (1996).

(Continued)

*Primary Examiner*—Mary K Zeman
(74) *Attorney, Agent, or Firm*—McDermott Will & Emery LLP

(57) ABSTRACT

The invention provides a method for obtaining a binding compound for a protein family, wherein the members of the protein family bind a common ligand. The method includes the steps of (a) providing a sample containing a protein from the protein family, a first ligand and a second ligand under conditions wherein the first ligand, the second ligand and the protein form a bound complex; (b) detecting magnetization transfer between the first ligand and the second ligand in the bound complex, thereby determining that the two ligands are proximal in the bound complex; and (c) obtaining a candidate binding compound including the first ligand, or a fragment thereof linked to the second ligand, or a homolog thereof, whereby the population contains binding compounds that bind to members of the protein family.

17 Claims, 12 Drawing Sheets

(2 of 12 Drawing Sheet(s) Filed in Color)

OTHER PUBLICATIONS

Blundell, T., "Structure-based drug design," *Nature*, 384 (6604 Supp) :23-26 (1996).

Borman, "Advance in NMR of Macromolecules; Technique makes it possible to obtain spectra of much larger proteins," *Chem. & Eng. News* 55-56 (1998).

Bull et al., "Mechanism-Based Inhibition of Human Steroid 5α-Reductase by Finasteride: Enzyme-Catalyzed Formation of NADP-Dihydrofinasteride, a Potent Bisubstrate Analog Inhibitor," *J. Am. Chem. Soc.*, 118:2359-2365 (1996).

Burke, T., "Protein-tyrosine kinase inhibitors," *Drugs of the Future*, 17:119-131 (1992).

Chen et al., "Biased Combinatorial Libraries: Novel Ligands for the SH3 Domain of Phosphatidylinositol 3-Kinase," *J. Am. Chem. Soc.*, 115:12591-12592 (1993).

Chen et al., "Mapping of the Binding Interfaces of the Proteins of the Bacterial Phosphotransferase System, HPr and IIA$^{glc}$," *Biochemistry* 32:32-37 (1993).

Cohen et al., "Modular Binding Domains in Signal Transduction Proteins," *Cell*, 80:237-248 (1995).

Combs et al., "Protein Structure-Based Combinatorial Chemistry: Discovery of Non-Peptide Binding Elements to Src SH3 Domain," *J. Am. Chem. Soc.*, 118:287-288 (1996).

Constantine et al., "Characterization of NADP$^+$Binding to Perdeuterated MurB: Backbone Atom NMR Assignments and Chemical-shift Changes," *J. Mol. Biol.*, 267:1223-1246 (1997).

Dalgarno et al., "SH3 Domains and Drug Design: Ligands, Structure, and Biological Function," *Biopoly*, 43:383-400 (1998).

Dalvit et al., "WaterLOGSY as a method for primary NMR screening: Practical aspects and range of applicability," *J. Biomol. NMR*, 21:349-359 (2001).

Dalvit, C., "Homonuclear 1D and 2D NMR Experiments for the Observation of Solvent-Solute Interactions," *J. Magn. Res.*, B112:282-288 (1996).

Dalvit, C., "Efficient multiple-solvent suppression for the study of the interactions of organic solvents with biomolecules," *J. Biomol. NMR*, 11:437-444 (1998).

Davey and Fenna, "2.3 Å Resolution X-ray Crystal Structure of the Bisubstrate Analogue Inhibitor Salicylhydroxamic Acid Bound to Human Myeloperoxidase: A Model for a Prereaction Complex with Hydrogen Peroxide," *Biochem.*, 35:10967-10973 (1996).

Davis et al., "Alterations in chemical shifts and exchange broadening upon peptide boronic acid inhibitor binding to α-lytic protease," *J. Biomolecular NMR*, 10:21-27 (1997).

Doucet and Weber, *Computer-Aided Molecular Design: Theory and Applications*, Academic Press, San Diego, 171-238 (1996).

Doucet and Weber, *Computer-Aided Molecular Design: Theory and Applications*, Academic Press, San Diego, 328-404 (1996).

Farmer et al., "Localizing the NADP$^+$ binding site on the MurB enzyme by NMR," *Nat. Structural Biol.*, 3:995-997 (1996).

Fejzo et al., "Dynamic NMR studies of ligand-receptor interactions: Design and analysis of a rapidly exchanging complex of FKBP-12/FK506 with a 24 kDa calcineurin fragment," *Protein Sci.*, 5:1917-1921 (1996).

Fejzo et al., "The SHAPES strategy: an NMR-based approach for lead generation in drug discovery," *Chemistry & Biology*, 6:755-769 (1999).

Feng et al., "Specific interactions outside the proline-rich core of two classes of Src homology 3 ligands," *Proc. Natl. Acad. Sci. USA*, 92:12408-12415 (1995).

Feng et al., "Molecular basis for the binding of SH3 ligands with non-peptide elements identified by combinatorial synthesis," *Chem. & Biol.*, 3:661-670 (1996).

Feng and Schreiber, "Enantiomeric Binding Elements Interacting at the Same Site of an SH3 Protein Receptor," *J. Am. Chem. Soc.*, 119:10873-10874 (1997).

Gray et al., "Exploiting Chemical Libraries, Structure, and Genomics in the Search for Kinase Inhibitors," *Science*, 281:533-538 (1998).

Hajduk et al., "Design of adenosine kinase inhibitors for the NMR-based screening of fragments," *J. Med. Chem.*, 43:4781 (2000).

Hajduk et al., "High-Throughput Nuclear Magnetic Resonance-Based Screening," *J. Med. Chem.*, 42:2315-2317 (1999).

Hajduk et al., "Discovery of Potent Nonpeptide Inhibitors of Stromelysin Using SAR by NMR," *J. Am. Chem. Soc.*, 119:5818-5827 (1997).

He et al., "Design and Synthesis of New Leads for PKC Bisubstrate Inhibitors," *Bioorganic & Medicinal Chemistry Letters*, 4:2845-2850 (1994).

Hrovat et al., "Backbone dynamics of oxidized and reduced *D. vulgaris* flavodoxin in solution," *J. Biomolecular NMR*, 10:53-62 (1997).

Ikeda et al., "Multisubstrate Analogs for Deoxynucleoside Kinases," *J. Biol. Chem.*, 261:15836-15843 (1986).

Kapoor et al., "Exploring the Specificity Pockets of Two Homologous SH3 Domains Using Structure-Based, Split-Pool Synthesis and Affinity-Based Selection," *J. Am. Chem. Soc.*, 120:23-29 (1998).

Kuntz et al., "A geometric approach to macromolecule-ligand interactions," *J. Mol. Biol.*, 161:269-288 (1982).

Labrou et al., "Molecular Modeling for the Design of a Biomimetic Chimeric Ligand. Application to the Purification of Bovine Heart L-Lactate Dehydrogenase," *Biotechnol. Bioeng.*, 63:322-332 (1999).

Labrou et al., "Molecular modelling for the design of chimaeric biomimetic dye-ligands and their interaction with bovine heart mitochondrial malate dehydrogenase," *Biochem. J.*, 315:695-703 (1996).

Labrou and Clonis, "Oxaloacetate Decarboxylase: On the Mode of Interaction with Substrate-Mimetic Affinity Ligands," *Arch. Biochem. Biophys.*, 321:61-70 (1995).

Labrou and Clonis, "The Interaction of *Candida boidinii* Formate Dehydrogenase with a New Family of Chimeric Biomimetic Dye-Ligands," *Arch. Biochem. Biophys.*, 316:169-178 (1995).

Labrou and Clonis, "Biomimetic-dye affinity chromatography for the purification of mitochondrial L-malate dehydrogenase from bovine heart," *J. Biotechnol.*, 45:185-194 (1996).

Lee et al., "Rapid corepressor exchange from the *trp*-repressor/operator complex: An NMR study of [ul-$^{13}$C/$^{15}$N] -L-tryptophan," *J. Biomol. NMR*, 5:367-375 (1995).

LeMaster, D., "Deuteration in Protein Proton Magnetic Resonance," *Methods Enzymol.*, 177:23-43 (1989).

Levitzki, A., "Tyrphostins: tyrosine kinase blockers as novel antiproliferative agents and dissectors of signal transduction," *FASEB J.*, 6:3275-3282 (1992).

Li et al., "The inter-ligand Overhauser effect: A powerful new NMR approach for mapping structural relationships of macromolecular ligands," *J. Biomol. NMR*, 15:71-76 (1999).

Martin, Y., "3D Database Searching in Drug Design," *J. Med. Chem.*, 35:2145-2154 (1992).

Medzihradszky et al., "Solid-Phase Synthesis of Adenosine Phosphopeptides as Potential Bisubstrate Inhibitors of Protein Kinases," *J. Am. Chem. Soc.*, 116:9413-9419 (1994).

Moore, J., "NMR Techniques for Characterization of Ligand Binding: Utility for Lead Generation and Optimization in Drug Discovery," *Biopoly*, 51:221-243 (1999).

Moore, J., "NMR screening in drug discovery," *Curr. Opin. Biotechnol.*, 10:54-58 (1999).

Morken et al., "Exploring the Leucine-Proline Binding Pocket of the Src SH3 Domain Using Structure-Based, Split-Pool Synthesis and Affinity-Based Selection," *J. Am. Chem. Soc.*, 120:30-36 (1998).

Muchmore et al., "Expression and Nitrogen-15 Labeling of Proteins for Proton and Nitrogen-15 Nuclear Magnetic Resonance," *Methods Enzymol.*, 177:44-73 (1989).

Ni et al., "Recent Developments In Transferred NOE Methods," *Proq. NMR Spect.*, 26:517-606 (1994).

Page and Jencks, "Entropic Contributions to Rate Accelerations in Enzymic and Intramolecular Reactions and the Chelate Effect," *Proc. Natl. Acad. Sci. USA*, 68:1678-1683 (1971).

Patel et al., "Phosphinyl Acid-Based Bisubstrate Analog Inhibitors of Ras Farnesyl Protein Transferase," *J. Med. Chem.*, 38:435-442 (1995).

Patel et al., "Phenol based Tripeptide Inhibitors of Ras Farnesyl Protein Transferase," *Bioorganic & Medicinal Chem. Letters*, 4:1883-1888 (1994).

Pawson, T., "Protein modules and signaling networks," *Nature*, 373:573-580 (1995).

Pervushin et al., "Attenuated T₂ relaxation by mutual cancellation of dipole-dipole coupling and chemical shift anisotropy indicates an avenue to NMR structures of very large biological macromolecules in solution," *Proc. Natl. Aad. Sci. USA*, 94:12366-12371 (1997).

Pervushin et al., "Transverse Relaxation-Optimized Spectroscopy(TROSY) for NMR Studies of Aromatic Spin Systems in $^{13}$C-Labeled Proteins," *J. Am. Chem. Soc.*, 120:6394-6400 (1998).

Radzicka and Wolfenden, "Transition state and multisubstrate analog inhibitors," *Methods in Enzymology* 249:284-303 (1995).

Reilly and Fairbrother, "A novel isotope labeling protocol for bacterially expressed proteins," *J. Biomolecular NMR*, 4:459-462 (1994).

Reinstein et al., "Fluorescence and NMR Investigations on the Ligand Binding Properties of Adenylate Kinases," *Biochem.*, 29:7440-7450 (1990).

Rickles et al., "Phage display selection of ligand residues important for Src homology 3 domain binding specificity," *Proc. Natl. Acad. Sci. USA*, 92:10909-10913 (1995).

Rossman et al., "Evolutionary and Structural Relationships Among Dehydrogenases," *The Enzymes*, 11:61-102 (1975).

Rozwarski et al., "Modification of the NADH of the Isoniazid Target (InhA) from *Mycobacterium tuberculosis*," *Science*, 279:98-102 (1998).

Salzmann et al., "TROSY-type Triple-Resonance Experiments for Sequential NMR Assignments of Large Proteins," *J. Am. Chem. Soc.*, 121:844-848 (1999).

Scheffzek et al., "Crystal Structure of the Complex of UMP/CMP Kinase from *Dictyostelium discoideum* and the Bisubstrate Inhibitor $P^1$-(5'-Adenosyl) $P^5$-(5'-Uridyl) Pentaphosphate (UP$_5$A) and Mg$^{2+}$ at 2.2 Å: Implications for Water-Mediated Specificity," *Biochem.*, 35:9716-9727 (1996).

Sem and Kasper, "Geometric Relationship between the Nicotinomide and Isoalloxazine Rings in NADPH-Cytochrome P-450 Oxidoreductase: Implications for the Classification of Evolutionarily and Functionally Related Flavoproteins," *Biochemistry*, 31:3391-3398 (1992).

Sem et al., "NMR Spectroscopic Studies of the DNA-binding Domain of the Monomer-binding Nuclear Orphan Receptor, Human Estrogen Related Receptor-2," *J. Biological Chem.*, 272:18038-18043 (1997).

Sem and Coutts, "Accelerating Drug Discovery at Triad Biotechnology," *Solutions*, pp. 9-11 (1998).

Shuker et al., "Discovering High-Affinity Ligands for Proteins: SAR by NMR," *Science*, 274:1531-1534 (1996).

Sikorski et al., "EPSP Synthase: The Design and Synthesis of Bisubstrate Inhibitors Incorporating Novel 3-Phosphate Mimics," *Phosphorus, Sulfur, and Silicon*, 76:115-118 (1993).

Suyama et al., "Searching for common sequence patterns among distantly related proteins," *Protein Engineering*, 8:1075-1080 (1995).

Tartar et al., "Design of PKC Inhibitors," *Actual. Chim. Thér.*, 18:167-180 (1991).

Traxler et al., "Sulfonylbenzoyl-Nitrostyrenes: Potential Bisubstrate Type Inhibitors of the EGF-Receptor Tyrosine Protein Kinase," *J. Med. Chem.*, 34:2328-2337 (1991).

van Nuland et al., "The NMR determination of the IIA$^{mtl}$ binding site on HPr of the *Escherichia coli* phosphoenol pyruvate-dependent phosphotransferase system," *FEBS*, 315:11-15 (1993).

Venters et al., "Characterizing the Use of Perdeuteration in NMR Studies of Large Proteins: $^{13}$C, $^{15}$N And $^1$H Assignments of Human Carbonic Anhydrase II," *J. Mol. Biol.*, 264:1101-1116 (1996).

Venters et al., "High-level $^2$H/$^{13}$C/$^{15}$N labeling of proteins for NMR studies," *J. Biomol. NMR* 5:339-344 (1995).

Wemmer and Williams, "Use of Nuclear Magnetic Resonance in Probing Ligand-Macromolecule Interactions," *Methods Enzymol.*, 239:739-767 (1994).

Wierenga et al., "Prediction of the Occurrence of the ADP-binding βαβ-fold in Proteins, Using an Amino Acid Sequence Fingerprint," *J. Mol. Biol.*, 187:101-107 (1986).

Wimalasena et al., "Chiral Multisubstrate Inhibitors of Dopamine β-Monoxygenase: Evidence for Dual Modes of Interaction," *Biochem.*, 36:7144-7153 (1997).

Wittekind et al., "Orientation of Peptide Fragments from Sos Proteins Bound to the N-Terminal SH3 Domain of Grb2 Determined by NMR Spectroscopy," *Biochem.*, 33:13531-13539 (1994).

Wüthrich, K., "The second decade-into the third millenium," *Nature Structural Biology*, NMR Supplement:492-495 (1998).

Yamazaki et al., "A Suite of Triple Resonance NMR Experiments for the Backbone Assignment of $^{15}$N, $^{13}$C, $^2$H Labeled Proteins with High Sensitivity," *J. Am. Chem. Soc.*, 116:11655-11666 (1994).

Yan and Lawrence, "Distinguishing between Closely Related Protein Kinases: A Variation on the bisubstrate Inhibitor Theme," *J. Am. Chem. Soc.*, 118:6321-6322 (1996).

Dalvit, "Identification of compounds with binding affinity to proteins via magnetization transfer from bulk water," *J. Biomol. NMR*, 18:65-68 (2000).

* cited by examiner

NUCLEAR MAGNETIC RESONANCE ASSEMBLY OF CHEMICAL ENTITIES

This application is based on, and claims the benefit of, U.S. Provisional Application No. 60/322,574, filed Sep. 10, 2001, and U.S. Provisional Application No. 60/340,219, filed Dec. 13, 2001, both of which are incorporated herein by reference.

BACKGROUND OF THE INVENTION

The present invention relates generally to drug discovery methods and, more specifically to Nuclear Magnetic Resonance (NMR) methods for identifying compounds that interact with macromolecules.

Two general approaches have traditionally been used for drug discovery: structure-based drug design and screening for lead compounds. Structure-based drug design utilizes a three-dimensional structure model of a drug target to predict or simulate interactions with known or hypothetical compounds. Alternatively, in cases where a three-dimensional structure model of a drug target complexed with a ligand is available, therapeutic drugs can be designed to mimic the structural properties of the ligand, thereby identifying lead compounds for further development.

Screening for lead compounds is another approach that has been used with some success to identify lead compounds for therapeutic targets. Screening involves assaying a library of candidate compounds to identify lead compounds that interact with a drug target. The probability of identifying a lead compound can be increased by providing increased numbers and variety of candidate compounds in the library to be screened. Synthetic methods are available for creating libraries of compounds and include, for example, combinatorial chemistry approaches in which selected chemical groups are variously combined to generate a library of candidate compounds having diverse combinations of the selected chemical groups. In addition, advances have been made to increase the through-put for a number of screening methods. However, for many drug targets the throughput of available screens is prohibitively low. Furthermore, even in cases where high throughput detection is available, limitations on available resources for obtaining a library with sufficient size or diversity, or for obtaining a sufficient quantity of the drug target to support a large screen, can be prohibitive.

The efficiency of library screening approaches can be increased by combining structure-based drug design with the methodologies currently available for library screening. In particular, the probability of identifying a lead compound in a screening approach can be increased by using focused libraries containing member compounds having a higher probability of interacting with the drug target. Focused libraries having members with a limited range of structural or functional variations have been obtained based on variations predicted from structure-based drug design methods and used to screen for candidate drugs.

However, for many drug targets of interest, three-dimensional structure models are not presently available. Although methods for structure determination are evolving, it is currently difficult, costly and time consuming to determine the structure of a macromolecule drug target at sufficient resolution to render structure-based drug design practical. It can often be even more difficult to produce a macromolecule-ligand complex in a condition allowing a sufficiently resolved structure model of the complex. The typically long time period required to obtain structure information useful for developing drug candidates is particularly limiting with regard to exploiting the growing number of potential drug targets identified by genomics research.

Thus, there exists a need for methods to reduce the size and diversity of candidate libraries required to screen for lead compounds. The present invention satisfies this need and provides related advantages as well.

SUMMARY OF THE INVENTION

The invention provides a method for obtaining a focused library of candidate binding compounds for a protein family, wherein the members of the protein family bind a common ligand. The method includes the steps of (a) observing competitive binding of the common ligand and a first ligand to a protein, wherein the protein is a member of the protein family, thereby determining that the first ligand binds to the common ligand binding site of the protein; (b) providing a sample containing the protein, a first ligand and a second ligand under conditions wherein the first ligand, the second ligand and the protein form a bound complex; (c) detecting magnetization transfer between the first ligand and the second ligand in the bound complex, thereby determining that the two ligands are proximal in the bound complex; and (d) obtaining a population of candidate binding compounds including the first ligand, or a fragment thereof, linked to one of a plurality of second ligand homologs, whereby the population contains binding compounds that bind to members of the protein family.

The invention further provides a method for obtaining a focused library of candidate binding compounds, wherein the members of the protein family bind a common ligand. The method includes the steps of (a) providing a plurality of samples containing the protein and a first ligand under conditions wherein the first ligand and the protein form a bound complex, wherein the protein is a member of a family of proteins that bind a common ligand; (b) assaying a population of candidate second ligands for the ability to transfer magnetization to the first ligand in a sample from the plurality; (c) identifying, from the population of candidate second ligands, a second ligand that transfers magnetization to the first ligand, thereby determining that the two ligands are proximal to each other in a ternary bound complex with the protein; (d) observing competitive binding between one of the two ligands and the common ligand, thereby determining that the competitive binding ligand binds to the common ligand binding site of the protein; and (e) obtaining a population of candidate binding compounds including the competitive binding ligand, or a fragment thereof, linked to one of a plurality of homologs of the other ligand, whereby the population of candidate binding compounds contains binding compounds that bind to members of the protein family.

The invention further provides a method for obtaining a focused library of candidate binding compounds for a protein family, wherein the members of the protein family bind a common ligand. The method includes the steps of: (a) providing a ligand-probe having an antenna moiety, wherein the ligand-probe binds to the common ligand binding site of a protein, wherein the protein is a member of the protein family; (b) providing a sample containing the protein, the ligand-probe and a second ligand under conditions wherein the ligand-probe, the second ligand and the protein form a bound complex; (c) detecting magnetization transfer between the antenna moiety of the ligand-probe and the second ligand in the bound complex, thereby determining that the antenna moiety and second ligand are proximal in the bound complex; and (d) obtaining a population of candidate binding compounds comprising the ligand-probe, or a fragment thereof, linked to one of a plurality of second ligand homologs, whereby the population contains binding compounds that bind to members of the protein family.

Also provided is a method for obtaining a focused library of candidate binding compounds, wherein the members of the protein family bind a common ligand. The method includes the steps of: (a) providing a ligand-probe having an antenna moiety, wherein the ligand-probe binds to the common ligand binding site of a protein, wherein the protein is a member of the protein family; (b) providing a plurality of samples containing the protein and the ligand-probe under conditions wherein the ligand-probe and the protein form a bound complex, wherein the protein is a member of a family of proteins that bind a common ligand; (c) assaying a population of candidate second ligands for the ability to transfer magnetization to the antenna moiety of the ligand-probe in a sample from the plurality; (d) identifying, from the population of candidate second ligands, a second ligand that transfers magnetization to the antenna moiety of the ligand-probe, thereby determining that the two ligands are proximal to each other in a ternary bound complex with the protein; and (e) obtaining a population of candidate binding compounds comprising the ligand-probe, or a fragment thereof, linked to one of a plurality of homologs of the other ligand, whereby the population of candidate binding compounds contains binding compounds that bind to members of the protein family.

Further provided is a method for identifying a compound having specificity for a particular member of a protein family, compared to other members of the protein family, prior to synthesizing the compound. The method includes the steps of: (a) observing competitive binding of the common ligand and a first ligand to a first protein, (b) observing competitive binding of the common ligand and a first ligand to a second protein, wherein the first and second proteins are members of the protein family, thereby determining that the first ligand binds to the common ligand binding site of the first and second proteins; (c) providing a sample containing the first protein, the first ligand and a second ligand; (d) providing a sample containing the second protein, the first ligand and the second ligand; (e) comparing the degree of magnetization transfer between the first ligand and the second ligand for the samples of parts (b) and (c); and (f) obtaining a binding compound including the first ligand, or a fragment thereof, linked to the second ligand, or a fragment thereof, whereby the binding compound selectively binds the first protein compared to the second protein.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
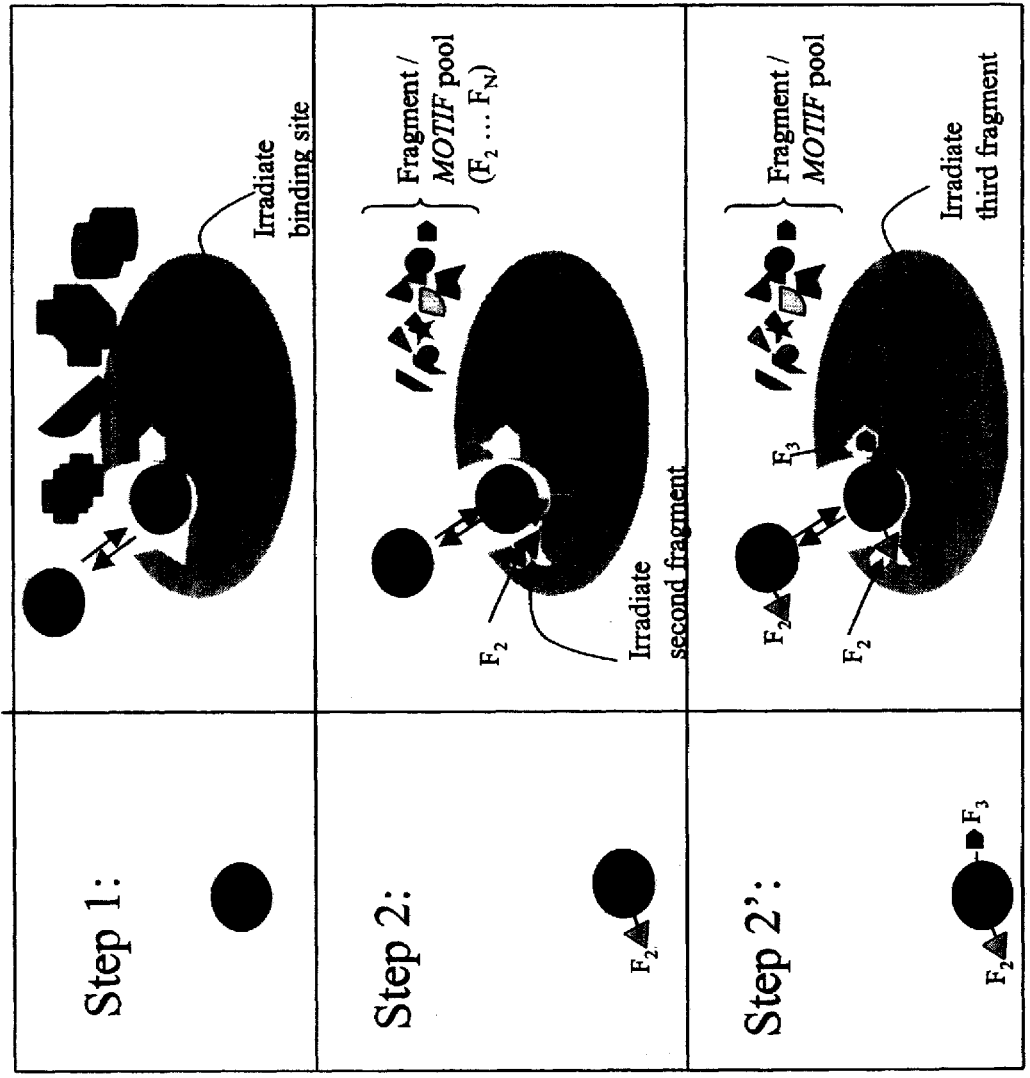
FIG. 1 shows a schematic diagram of a method for sequentially building a binding compound from three ligands.

This invention provides a method for identifying a compound that will bind to a macromolecule. Using a method of the invention, the relative positions of two or more ligands when bound to a macromolecule in a multipartite complex can be determined. Based on this determination, the ligands or portions of the ligands can be covalently linked to form a binding compound. An advantage of the invention is that atomic-resolution structural data for a macromolecule, although useful in some aspects of the invention, is not necessary in order to obtain a compound that binds to the macromolecule.

The methods can also be used to design a library that is focused toward members of a particular protein family having a common ligand site (CLS). The focused library can include compounds with various combinations of linked moieties, where the moieties are structurally similar to each ligand observed in a multipartite complex and the linker between the moieties is selected based on the relative positions of the ligands in the multipartite complex. A focused library can be designed by determining the relative positions of two or more ligands when bound to a macromolecule in a multipartite complex, identifying which of the ligands is a common ligand capable of binding to the CLS and building the library to contain members having the common ligand linked to various moieties that are structurally similar to the other ligand. An advantage of the invention is that screening with one or a representative subset of proteins in a family can be used to design a library that is focused with respect to other proteins in the family.

Nuclear Magnetic Resonance (NMR) can be used in a method of the invention to determine the relative proximity or positions of ligands in a multipartite complex with a macromolecule. In particular, proximal ligands can be identified from NMR-based observation of magnetization transfer between the ligands. Although NMR methods have been previously used to predict or determine the structure of ligands bound to macromolecules, these methods have relied upon detection of magnetic interactions between the ligand and the macromolecule. Isotopic labeling can be required for macromolecules in order to detect magnetic interactions with a bound ligand. Furthermore, for many large or membrane bound macromolecules signal broadening, due in part to low rotational mobility, renders detection of magnetic interactions with ligands impractical. Because the methods of the present invention are based on detection of interactions between ligands and do not require detection of interactions with macromolecule, isotopically labeled macromolecules are not necessary. The methods are further advantageous for use with large or membrane bound macromolecules because observation of magnetization transfer between ligands can be enhanced when the ligands experience low rotational mobility.

A further advantage of the invention is that ligands having relatively low affinities for a macromolecule can be identified and linked to form a compound having substantially increased affinity for the macromolecule. Such increased affinity is expected to occur, for example, due to the chelate effect (for a description of the chelate effect see Page et al., Proc. Natl. Acad. Sci. USA 68:1678-1683 (1971)) and is demonstrated in the Examples below. Another advantage of the invention is that a compound having increased specificity for a particular macromolecule, compared to a ligand from which it is assembled, can be identified. In particular, members of a CLS-containing protein family often have a different specificity ligand site adjacent to the common ligand binding site which provides a potential source of binding specificity (as described, for example, in U.S. patent application Ser. No. 09/328,322 and WO 99/60404). By linking the common ligand to a particular specificity ligand, a compound can be obtained that has increased affinity due to the presence of both ligands and increased specificity for a particular member of a protein family compared to the common ligand.

A ligand can include an antenna moiety that extends from the core structure of the ligand to interact with a proximal ligand. An antenna moiety can extend the range within which a proximal ligand is identified. The use of a multi-probe ligand having multiple antennas or comparison of ligands having antennas of different composition or point of attachment on the ligand moiety can provide information on the relative orientation of the proximal ligands and their binding sites. Because the methods of the invention provide not only a functional identification that a ligand binds to a macromolecule, but also identify the relative positions of two ligands when bound to the macromolecule, the invention provides structural information. Use of a method of the invention in a screening format provides a way to increase the throughput at which structural information can be obtained on the relative orientation of the proximal ligands and their binding sites.

In the following description, for the purposes of explanation, specific details are set forth in order to provide a thorough understanding of the present invention. Those skilled in the art will understand that the present invention can be practiced without these specific details and can be applied to any of a variety of related systems. For example, although the methods are described in the context of ligands that bind to a protein, it is understood that the methods can be applied to other macromolecules including, for example, synthetic polymers, DNA, RNA or polysaccharides that interact with ligands.

As used herein, the term "ligand" is intended to mean a molecule that can form a specific, non-covalent association with a macromolecule. A molecule included in the term can be a small molecule, a binding compound or a macromolecule. A molecule included in the term can be naturally occurring such as a DNA, RNA, polypeptide, protein, lipid, carbohydrate, amino acid, nucleotide, metabolite or hormone; a synthetic molecule; or a derivative of a naturally occurring molecule. A derivative can have, for example, an added moiety, a removed moiety or a rearrangement in the relative location of moieties compared to a naturally occurring molecule. As used herein, the term "binding compound" is intended to mean a ligand having a covalent structure that includes at least two moieties that interact with a macromolecule.

As used herein, the term "binding site" is intended to mean a portion of a macromolecule or complex of macromolecules that associates specifically and non-covalently with a ligand or portion of a ligand. A non-covalent association included in the term can be due to a hydrogen bond, ionic interaction, van der Waals interaction, or hydrophobic interaction or a combination thereof.

As used herein, the term "competitive binding" is intended to mean binding of a first ligand to a binding site of a macromolecule in a manner that prevents a second ligand from binding to the binding site. Accordingly, a first and second ligand that bind to a binding site of a macromolecule in a mutually exclusive manner are understood to be competitive inhibitors of each other for the macromolecule.

As used herein, the term "bound complex" is intended to mean a specific non-covalent association between 2 or more molecules. The term can include a reversible association so long as the association is sufficiently stable to be observed by a binding assay.

As used herein, the term "common ligand" or "CL" is intended to mean a molecule that specifically binds at a site conserved in a family of 2 or more macromolecules. The term can therefore extend to molecules that bind to members of a protein family or gene family. Examples of common ligands include a natural common ligand which is normally found in biological systems or a common ligand mimic which has sufficient structural similarity to a natural common ligand that it can competitively inhibit binding of the natural common ligand to its common ligand binding site. Accordingly, a "common ligand site" is intended to mean a location in or on a macromolecule where a common ligand binds. A common ligand site is also referred to as a conserved site.

The term "mimic," when used in reference to a ligand, is intended to mean a molecule that binds to a protein at the same site as the ligand. The term can encompass molecules having portions similar to corresponding portions of the ligand in terms of structure or function. The term can also encompass the original ligand itself.

An example of a useful CL is a cofactor or a cofactor mimic. A "cofactor" is any small molecule that binds in the CL site and participates in catalysis when bound to an enzyme. Cofactors often contain a nucleotide such as adenine mononucleotide or nicotinamide mononucleotide. Examples of such cofactors include ATP, ADP and SAM (S-adenosyl methionine). Another group of cofactors that contain a nucleotide is the group $NAD^+$, NADH, $NADP^+$ and NADPH. Other such cofactors include $FMNH_2$, FMN, FAD, $FADH_2$, CoA, GTP and GDP. Still other cofactors include THF, DHF, TPP, biotin, dihydropterin, heme, pyridoxal phosphate and thiamine pyrophosphate. Other common ligands include conserved ligands such as farnesyl, farnesyl-pyrophosphate, geranyl, geranyl-pyrophosphate or ubiquitin.

As used herein, the term "family," when used in reference to a macromolecule, is intended to mean a group of at least 2 macromolecules exhibiting structure homology and at least one function in common. An exemplary function included in the term is the ability to bind a common ligand such as NADH or ATP. Examples of enzyme families include kinases, dehydrogenases, oxidoreductases, GTPases, carboxyl transferases, acyl transferases, decarboxylases, transaminases, racemases, methyl transferases, formyl transferases, and α-ketodecarboxylases. As used herein, the term "enzyme" refers to a molecule that binds a substrate ligand and carries out a catalytic reaction by converting the substrate ligand to a product.

Enzymes can also be classified based on Enzyme Commission (EC) nomenclature recommended by the Nomenclature Committee of the International Union of Biochemistry and Molecular Biology (IUBMB) and available from the ENZYME database. (available on the internet at expasy.ch/enzyme/; administered by The Swiss Institute for Bioinformatics, Switzerland; see, for example, Bairoch, *Nucl. Acid. Res.* 28:304-305 (2000)). For example, oxidoreductases are classified as oxidoreductases acting on the CH—OH group of donors with $NAD^+$ or $NADP^+$ as an acceptor (EC 1.1.1); oxidoreductases acting on the aldehyde or oxo group of donors with $NAD^+$ or $NADP^+$ as an acceptor (EC 1.2.1); oxidoreductases acting on the CH—CH group of donors with $NAD^+$ or $NADP^+$ as an acceptor (EC 1.3.1); oxidoreductases acting on the $CH-NH_2$ group of donors with $NAD^+$ or $NADP^+$ as an acceptor (EC 1.4.1); oxidoreductases acting on the CH—NH group of donors with $NAD^+$ or $NADP^+$ as an acceptor (EC 1.5.1); oxidoreductases acting on NADH or NADPH (EC 1.6); and oxidoreductases acting on NADH or NADPH with $NAD^+$ or $NADP^+$ as an acceptor (EC 1.6.1).

Additional oxidoreductases include oxidoreductases acting on a sulfur group of donors with $NAD^+$ or $NADP^+$ as an acceptor (EC 1.8.1); oxidoreductases acting on diphenols and related substances as donors with $NAD^+$ or $NADP^+$ as an acceptor (EC 1.10.1); oxidoreductases acting on hydrogen as donor with $NAD^+$ or $NADP^+$ as an acceptor (EC 1.12.1); oxidoreductases acting on paired donors with incorporation of molecular oxygen with NADH or NADPH as one donor and incorporation of two atoms (EC 1.14.12) and with NADH or NADPH as one donor and incorporation of one atom (EC 1.14.13); oxidoreductases oxidizing metal ions with $NAD^+$ or $NADP^+$ as an acceptor (EC 1.16.1); oxidoreductases acting on —$CH_2$ groups with $NAD^+$ or $NADP^+$ as an acceptor (EC 1.17.1); and oxidoreductases acting on reduced ferredoxin as donor, with $NAD^+$ or $NADP^+$ as an acceptor (EC 1.18.1).

Other enzymes include transferases classified as transferases transferring one-carbon groups (EC 2.1); methyltransferases (EC 2.1.1); hydroxymethyl-, formyl- and related transferases (EC 2.1.2); carboxyl- and carbamoyltransferases (EC 2.1.3); acyltransferases (EC 2.3); and transaminases (EC 2.6.1). Additional enzymes include phosphotransferases such as phosphotransferases transferring phosphorous-containing groups with an alcohol as an acceptor (kinases) (EC 2.7.1); phosphotransferases with a carboxyl group as an acceptor (EC 2.7.2); phosphotransfer with a nitrogenous group as an acceptor (EC 2.7.3); phosphotransferases with a phosphate group as an acceptor (EC 2.7.4); and diphosphotransferases (EC 2.7.6).

Protein or gene family members can often be identified by the presence of a conserved structural motif as described, for example, in Branden and Tooze *Introduction to Protein Structure*, Garland Publishing Inc., New York (1991). A structural motif can be identified at the primary structure level according to a particular nucleotide or amino acid sequence or at the tertiary structure level due to a particular combination or orientation of secondary structure elements. Identification of structural motifs using structural alignments is described in further detail below.

Several large protein and gene families have been identified, including families having as many as 20 or more, 50 or more, 100 or more and even 200 or more members. Two particular examples of a protein or gene family are kinases and oxidoreductases. The term "kinase" herein means any enzyme that catalyzes the transfer of a phosphoryl group from ATP or other nucleoside triphosphate to another compound. The term "oxidoreductase" herein means any enzyme that catalyzes an oxidation-reduction reaction. Still other gene families include transaminases, decarboxylases and methyltransferases.

Another particular gene family is the dehydrogenase gene family. The term "dehydrogenase" herein means any enzyme that catalyzes the removal of hydrogen from a substrate using a compound other than molecular oxygen as an acceptor. Typically the hydrogen is transferred to the coenzyme $NAD^+$ (nicotinamide adenine dinucleotide) or $NADP^+$ (nicotinamide adenine dinucleotide phosphate). The dehydrogenase gene family is large, containing approximately 17% of all enzymes (You, Kwan-sa, "Stereospecificity for Nicotinamide Nucleotides in Enzymatic and Chemical Hydride Transfer Reactions," *CRC Crit. Rev. Biochem.* 17:313-451 (1985)). Thus, the dehydrogenase family is likely to be a rich source of drug targets.

As used herein, the term "specificity" refers to the ability of a ligand to selectively bind to one macromolecule over another. For example, the term can include selective binding of a ligand to one member of a protein family compared to other proteins outside of or within the protein family. The selective binding of a particular ligand to a macromolecule is measurably higher than the binding of the ligand to at least one other molecule. Specificity can also be exhibited over two or more, three or more, four or more, five or more, six or more, seven or more, ten or more, or even twenty or more other macromolecules.

As used herein, the term "structure model" is intended to mean a representation of the relative locations of atoms of a molecule. A representation included in the term can be defined by a coordinate system that is preferably in 3 dimensions, however, manipulation or computation of a model can be performed in 2 dimensions or even 4 or more dimensions in cases where such methods are desired. The location of atoms in a molecule can be described, for example, according to bond angles, bond distances, relative locations of electron density, probable occupancy of atoms at points in space relative to each other, probable occupancy of electrons at points in space relative to each other or combinations thereof. A representation included in the term can contain information for all atoms of a particular molecule or a subset of atoms thereof. Examples of representations included in the term that contain a subset of atoms are those commonly used for polypeptide structures such as ribbon diagrams, and the like, which show the coordinates of the polypeptide backbone while omitting coordinates for all or a portion of the side chain moieties of the polypeptide. Representations for other macromolecules and small molecules included in the term can similarly contain all or a subset of atoms.

A structure model can include a representation that is determined from empirical data derived from, for example, X-ray crystallography or nuclear magnetic resonance spectroscopy. A representation included in the term can include one that is derived from a theoretical calculation including, for example, a structure obtained by homology modeling or ab initio modeling. A representation of a structure model can include, for example, an electron density map, atomic coordinates, x-ray structure model, ball and stick model, density map, space filling model, surface map, Connolly surface, Van der Waals surface or CPK model.

As used herein, the term "docking" is intended to mean using a model of a first and second molecule to simulate association of the first and second molecule at a proximity sufficient for at least one atom of the first molecule to be within bonding distance of at least one atom of the second molecule. The term is intended to be consistent with its use in the art pertaining to molecular modeling. A model included in the term can be any of a variety of known representations of a molecule including, for example, a graphical representation of its three-dimensional structure, a set of coordinates, set of distance constraints, set of bond angle constraints or set of other physical or chemical properties or combinations thereof.

As used herein, the term "magnetization transfer" is intended to mean a through-space alteration of the nuclear magnetic resonance properties of an atomic nucleus of a first atom due to a proximal atomic nucleus or at least one electron of a proximal atom. An alteration included in the term can occur due to the Nuclear Overhauser Effect (NOE) or cross saturation. Proximal atomic nuclei included in the term are those that are within a distance sufficient to cause a magnetic interaction detectable by a nuclear magnetic resonance spectroscopy measurement used in the methods of the invention. Examples of magnetic effects included in the term are a relaxation effect which can be detected for atoms that are about 10 Å apart or closer, the Nuclear Overhauser Effect which can be detected for atoms that are about 6 Å apart or closer or chemical shift due to shielding or de-shielding which can be detected for atoms that are about 10 Å or closer. Atoms that are about 5 Å apart or closer, 4 Å apart or closer, 3 Å apart or closer, 2 Å apart or closer or 1 Å apart or closer are also proximal atoms that are included in the term.

As used herein, the term "linker" is intended to mean one or more atoms that covalently connect a first moiety to a second moiety. A moiety included in the term can be a ligand such as a common ligand, or fragment thereof; a specificity ligand, or fragment thereof; or a mimic of a common ligand or specificity ligand. A linker can provide positioning and orientation of a first moiety relative to a second moiety such that one moiety can bind to a first ligand site and the other moiety can bind to a second, proximal site on a macromolecule.

As used herein, a "library" is intended to mean a population of different molecules. The library is chemically synthesized and contains primarily the components generated during the synthesis. A population included in the term can include two or more different molecules. A population can be as large as the number of individual molecules currently available to the user or able to be made by one skilled in the art. A population can be as small as two molecules and as large as $10^{10}$ molecules. Generally, a population will contain two or more, three or more, five or more, nine or more, ten or more, twelve or more, fifteen or more, or twenty or more different molecules. A population can also contain tens or hundreds of different molecules or even thousands of different molecules. For example, a population can contain about 20 to about 100,000 different molecules or more, for example about 25 or more, 30 or more, 40 or more, 50 or more, 75 or more, 100 or more, 150 or more, 200 or more, 300 or more, 500 or more, or 1000 or more different molecules, and particularly about 10,000, 100,000 or even $1\times10^6$ or more different molecules. A population of synthetic compounds can be derived, for example, by chemical synthesis and is substantially free of naturally occurring substances.

As used herein, the term "homolog" is intended to mean a molecule or moiety of a molecule that has similar structure in comparison to a reference molecule or moiety. A moiety is a group of atoms that form a part or portion of a larger molecule. A moiety can consist of any number of atoms in a portion of a molecule and can correlate with a physical or chemical property conferred upon the molecule by the combined atoms.

As used herein, the term "ligand-probe" is intended to mean a molecule that can selectively bind a protein and that has an antenna moiety and a ligand moiety. A "ligand moiety" is a fragment of a ligand-probe, that when lacking the antenna moiety, is capable of selectively binding to the protein. An "antenna moiety" is a structure containing an NMR-observable nucleus that is attached to a ligand moiety by bonding to at least 1 intervening atoms. A larger number of atoms can intervene between an NMR-observable nucleus and ligand moiety including, for example, at least 2, 3, 4, 5, 6, 7, 8, 9, 10 or more intervening atoms. The intervening atoms can form an aliphatic chain that, when attached to a ligand moiety having aromatic rings, allows selective excitation due to differences in frequency for excitation or saturation of aliphatic and aromatic protons. An NMR-observable nucleus of an antenna moiety can be a proton that is isolated from vicinal proton coupling. Isolation from vicinal proton coupling provides for selective observation of direct NOE transfer at short mixing times compared to indirect NOE transfer via spin diffusion and also reduces signal loss due to relaxation effects that occur for vicinal coupled protons. A proton can be isolated from vicinal proton coupling by being attached to a carbon that is adjacent to an atom that lacks protons including, for example, an ether oxygen; carbonyl carbon; thioether, sulfone or sulfoxide sulfur; deuterated carbon or selenium, or by being attached to a carbon that is adjacent to an atom having fast exchanging protons such as a nitrogen at high pH.

The invention provides a method for assembling a binding compound. The method includes the steps of (a) obtaining a sample containing a macromolecule, a first ligand and a second ligand under conditions wherein a bound complex is formed containing the first ligand, the second ligand and the macromolecule; (b) detecting magnetization transfer between the first ligand and the second ligand in the bound complex; (c) determining from the magnetization transfer the distance between an atom of the first ligand and an atom of the second ligand in the bound complex; and (d) obtaining a binding compound including the first ligand, or a fragment thereof, the second ligand, or a fragment thereof, and a linker, whereby the binding compound is capable of binding the macromolecule.

The invention further provides a method for obtaining a focused library of candidate binding compounds for a protein family, wherein the members of the protein family bind a common ligand. The method includes the steps of (a) observing competitive binding of the common ligand and a first ligand to a protein, wherein the protein is a member of the protein family, thereby determining that the first ligand binds to the common ligand binding site of the protein; (b) providing a sample containing the protein, a first ligand and a second ligand under conditions wherein the first ligand, the second ligand and the protein form a bound complex; (c) detecting magnetization transfer between the first ligand and the second ligand in the bound complex, thereby determining that the two ligands are proximal in the bound complex; and (d) obtaining a population of candidate binding compounds including the first ligand, or a fragment thereof, linked to one of a plurality of second ligand homologs, whereby the population contains binding compounds that bind to members of the protein family.

A schematic overview that exemplifies a method for assembling a binding compound is shown in FIG. 1. At step 1, a ligand, shown as $F_1$, is identified based on the observation that it binds to a protein. The binding can be observed based on magnetization transfer between the protein binding site and the $F_1$ ligand. The $F_1$ ligand can be obtained from a screen in which a library of candidate ligands are tested for the ability to bind the protein. At step 2, the $F_2$ ligand is identified as binding to the protein at a location that is proximal to the $F_1$ ligand. Proximal ligands can be identified based on the observation of magnetization transfer between the $F_1$ ligand and $F_2$ ligand when in a complex with the protein. The $F_2$ ligand can be identified from a screen using a library of candidate ligands. Based on the observed magnetization transfer a bi-ligand compound can be obtained in which the $F_1$ and $F_2$ ligands are linked. Alternatively, fragments or homologs of either ligand can be linked to form a bi-ligand. As shown in step 2', the bi-ligand compound can be used to identify a third proximal ligand, shown as ligand $F_3$, and a tri-ligand can be subsequently obtained in which the $F_1$, $F_2$ and $F_3$ ligands are linked. These and related methods are set forth in further detail below.

Initially, a macromolecule target such as a protein is identified for the development of a binding compound. In one embodiment, a macromolecule target for development of a therapeutic agent can be identified based on its presence in a pathogen or its association with a disease or condition. For example, a protein target present in a pathogen can be selected as the target to develop drugs effective in combating a disease caused by that pathogen. Any pathogen can be selected as a target organism. Examples of pathogens include, for example, bacteria, fungi or protozoa.

Pathogenic bacteria useful as target organisms include *Staphylococcus*, *Mycobacteria*, *Mycoplasma*, *Streptococcus*, *Haemophilus*, *Neisseria*, *Bacillus*, *Clostridium*, *Corynebacteria*, *Salmonella*, *Shigella*, *Vibrio*, *Campylobacter*, *Helicobacter*, *Pseudomonas*, *Legionella*, *Bordetella*, *Bacteriodes*, *Fusobacterium*, *Yersinia*, *Actinomyces*, *Brucella*, *Borrelia*, *Rickettsia*, *Ehrlichia*, *Coxiella*, *Chlamydia*, and *Treponema*. Pathogenic strains of *Escherichia coli* can also be target organisms.

Binding compounds targeted to macromolecules in these pathogenic bacteria are useful for treating a variety of diseases including bacteremia, sepsis, nosocomial infections, pneumonia, pharyngitis, scarlet fever, necrotizing fascitis, abscesses, cellulitis, rheumatic fever, endocarditis, toxic shock syndrome, osteomyelitis, tuberculosis, leprosy, meningitis, pertussis, food poisoning, enteritis, enterocolitis, diarrhea, gastroenteritis, shigellosis, dysentery, botulism, tetanus, anthrax, diphtheria, typhoid fever, cholera, actinomycosis, Legionnaire's disease, gangrene, brucellosis, lyme disease, typhus, spotted fever, Q fever, urethritis, vaginitis, gonorrhea and syphilis.

For example, *Staphylococcus aureus* is a major cause of nosocomial infections and has become increasingly resistant to a variety of antibiotics over recent years. Similarly, *Mycobacteria tuberculosis* has become increasingly resistant to multiple antibiotics in recent years. *M. tuberculosis* infects almost one third of the world population, with active tuberculosis found in almost 10 million people worldwide and in AIDS patients as a common opportunistic infection. *Streptomyces* has also become increasingly resistant to antibiotics over recent years. Therefore, these pathogenic bacteria with known resistance and target macromolecules required for their growth or pathogenesis are particularly desirable as target organisms for which therapeutic binding compounds can be identified.

In another embodiment, target organisms are selected from yeast and fungi. Pathogenic yeast and fungi useful as target organisms include *Aspergillus*, *Mucor*, *Rhizopus*, *Candida*, *Cryptococcus*, *Blastomyces*, *Coccidioides*, *Histoplasma*, *Paracoccidioides*, *Sporothrix*, and *Pneumocystis*. Binding compounds targeted to macromolecules in these pathogenic yeast and fungi are useful for treating a variety of diseases including aspergillosis, zygomycosis, candidiasis, cryptococcoses, blastomycosis, coccidioidomycosis, histoplasmosis, paracoccidioidomycosis, sporotrichosis, and pneuomocystis pneumonia.

In still another embodiment, target organisms are selected from protozoa. Pathogenic protozoa useful as target organisms include *Plasmodium*, *Trypanosoma*, *Leishmania*, *Toxoplasma*, *Cryptosporidium*, *Giardia*, and *Entamoeba*. Binding compounds targeted to macromolecules in these pathogenic protozoa are useful for treating a variety of diseases including malaria, sleeping sickness, Chagas' disease, leishmaniasis, toxoplasmosis, cryptosporidiosis, giardiasis, and amebiasis.

In addition, a target cell such as a cancer cell can be selected to identify drugs effective for treating cancer. Examples of such target cells include, for example, breast cancer, prostate cancer, and ovarian cancer cells as well as leukemia, lymphomas, melanomas, sarcomas and gliomas. Binding compounds directed to a target macromolecule in a cancer cell are useful for targeted delivering of a chemotherapeutic agent or for inhibition of unregulated growth. Diagnosis and identification of causative factors or pathogens for a targeted disease can be determined using methods known in the art as described for example in *The Merck Manual*, Sixteenth Ed, (Berkow, R., Editor) Rahway, N.J., 1992.

A macromolecule family to which a target macromolecule belongs can be identified according to structural or functional similarities using methods known in the art. Structural similarity can be identified, for example, by sequence analysis at the nucleotide or amino acid level. One method for determining if two macromolecules are related is BLAST, Basic Local Alignment Search Tool. (available on the internet at ncbi.nlm.nih.gov/BLAST/; administered by The National Center for Biotechnology Information, Bethesda Md.). BLAST is a set of similarity search programs designed to examine all available sequence databases and can function to search for similarities in protein or nucleotide sequences. A BLAST search provides search scores that have a well-defined statistical interpretation. Furthermore, BLAST uses a heuristic algorithm that seeks local alignments and is therefore able to detect relationships among sequences which share only isolated regions of similarity (Altschul et al., *J. Mol. Biol.* 215: 403-410 (1990)).

In addition to the originally described BLAST (Altschul et al., supra, 1990), modifications to the algorithm have been made (Altschul et al., *Nucleic Acids Res.* 25:3389-3402 (1997)). One modification is Gapped BLAST, which allows gaps, either insertions or deletions, to be introduced into alignments. Allowing gaps in alignments tends to reflect biologic relationships more closely. A second modification is PSI-BLAST, which is a sensitive way to search for sequence homologs. PSI-BLAST performs an initial Gapped BLAST search and uses information from any significant alignments to construct a position-specific score matrix, which replaces the query sequence for the next round of database searching. A PSI-BLAST search is often more sensitive to weak but biologically relevant sequence similarities.

A second resource for identifying members of a protein family is PROSITE. (Available on the internet at expasy.ch/sprot/prosite.html; administered by The Swiss Institute for Bioinformatics, Switzerland). PROSITE is a method of determining the function of uncharacterized proteins translated from genomic or cDNA sequences (Bairoch et al., *Nucleic Acids Res.* 25:217-221 (1997)). PROSITE consists of a database of biologically significant sites and patterns that can be used to identify which known family of proteins, if any, the new sequence belongs. In some cases, the sequence of an unknown protein is too distantly related to any protein of known structure to detect its resemblance by overall sequence alignment. However, related proteins can be identified by the occurrence in its sequence of a particular cluster of amino acid residues, which can be called a pattern, motif, signature or fingerprint. PROSITE uses a computer algorithm to search for motifs that identify proteins as family members. PROSITE also maintains a compilation of previously identified motifs, which can be used to determine if a newly identified protein is a member of a known protein family.

Members of a protein family can also be identified by clustering binding site structures or bound ligand conformations as described, for example, in U.S. patent application Ser. No. 10/040,895. A sequence model such as a Hidden Markov Model, representing the frequency and order with which specific amino acids or gaps occur in the binding sites of protein family members can be used to search a sequence database and identify other members as described, for example, in U.S. patent application Ser. No. 10/040,895. Members of a protein family can also be identified by clustering their sequence comparison signatures, where a sequence comparison signature for a protein is a string of pairwise comparison scores for the protein compared to the other proteins in a database as described, for example, in U.S. patent application Ser. No. 10/032,395.

Another resource for identifying members of a protein family is Structural Classification of Proteins (SCOP, Available on the internet at scop.mrc-lmb.cam.ac.uk/scop/, administered by Medical Research council, Cambridge, England. (which is incorporated herein by reference). SCOP maintains a compilation of previously determined protein tertiary folds from which structural comparison can be made to identify protein family members having similar motifs (Murzin et al., *J. Mol. Biol.* 247:536-540 (1995)).

TABLE 1

Databases for Identifying Protein Family Motifs

| | WEBSITES |
|---|---|
| SEARCHABLE MOTIF AND PATTERN DATABASES | |
| PROSITE | expasy.hcuge.ch/sprot/prosite.html |
| BLOCKS | blocks.fhcrc.org/blocks_search.html |
| PRINTS | biochem.ucl.ac.uk/bsm/dbbrowser/PRINTS/PRINTS.html |
| PIMA | dot.imgen.bcm.tmc.edu:9331/seq-search/protein-search.html |
| PRODOM | protein.toulouse.inra.fr/prodom.html |
| MOTIF AND PROFILE SEARCHES | |
| REGULAR EXPRESSION SEARCH | ibc.wustl.edu/fpat/ |
| PROFILESEARCH | seqnet.dl.ac.uk/hhg/PROFILESE.html |
| PATSCAN | c.mcs.ani.gov/home/overbeek/PatScan/HTML/patscan.html |

TABLE 1-continued

Databases for Identifying Protein Family Motifs

| | WEBSITES |
|---|---|
| PATTERNFIND | ulrec3.unil.ch/softwar e/PATFND-mailform.html |
| PROFILE | lenti.med.umn.edu/MolB io_man/chp-10.html#HDR1 |
| PMOTIF | alces.med.umn.edu/pmot if.html |
| HMMER | genome.wustl.edu/eddy/HMMER/ |
| WWW AND FTP SERVERS FOR SINGLE SEQUENCE EXHAUSTIVE DATABASE SEARCHES | |
| BLAST | ncbi.nlm.nih.gov/BLAST/ |
| BLITZ | ebi.ac.uk/searches/blitz_in put.html |
| FASTA | genome.ad.jp/ideas/fasta /fasta_genes.html |
| FTP ADDRESSES FOR MOTIF AND PROFILE SEARCH PROGRAMS | |
| BARTON'S FLEXIBLE PATTERNS | geoff.biop.ox.ac.uk/ |
| PROPAT | mdc-berlin.de/ |
| SOM | ftp.mdc-berlin.de/pub/neural |
| SEARCHWISE | sable.ox.ac.uk/pub/users |
| PROFILE | ftp.ebi.ac.uk/pub/soft ware/unix/ |
| TPROFILESEARCH | ftp.ebi.ac.uk/pub/soft are/vax/egcg |
| CAP | ncbi.nlm.nih.gov/pub/k oonin/cap |

Additional resources for identifying motifs of a protein family are shown in Table 1. The websites cited therein are incorporated by reference.

Conserved amino acids are evolutionarily conserved and carry out a common function. For example, the Rossman fold is a tertiary structural motif that includes GXXGXXG or GXGXXG and is present in enzymes that bind nucleotides (Brandon and Tooze, in *Introduction to Protein Structure*, Garland Publishing, New York (1991)). Enzymes that bind nucleotides such as NAD, NADP, FAD, ATP, ADP, AMP and FMN contain the Rossman fold sequence motif (Creighton, *Proteins: Structures and Molecular Principles*, p. 368, W. H. Freeman, New York (1984)). Additional conserved residues as well as different protein structures distinguish protein families that bind, for example, NAD from those that bind, for example, ATP.

An example of a recognizable protein motif or fingerprint is found in dinucleotide binding proteins such as dehydrogenases (Rossman et al., in *The Enzymes* Vol 11, Part A, 3rd ed., Boyer, ed., pp. 61-102, Academic Press, New York (1975); Wierenga et al., *J. Mol. Biol.* 187:101-107 (1986); and Ballamacina, *FASEB J.* 10:1257-1269 (1996)). The fingerprint region contains a phosphate binding consensus sequence GXXGXXG or GXGXXG, a hydrophobic core of six small hydrophobic residues, a conserved, negatively charged residue that binds to the ribose 2' hydroxyl of adenine and a conserved positively charged residue (Bellamacina, supra).

Protein kinases also have recognizable motifs conserved among all known protein kinases (Hanks and Quinn, *Methods Enzymol.* 200:28-62 (1991)). Eight invariant amino acid residues are conserved throughout the protein kinase family, including a conserved GXGXXG motif similar to that seen in dinucleotide binding proteins. A crystallographic molecular model of cyclic AMP-dependent protein kinase as well as other protein kinases showed that these conserved residues are nearly all associated with essential, conserved functions such as ATP binding and catalysis (Knighton et al., *Science* 253:407-414 (1991); and Knighton et al., *Science* 253:414-420 (1991)). Thus, conserved amino acid residues, which are common to members of a protein family, are recognizable as a motif critical for the structure, function or activity of a protein.

Pyridoxal binding proteins also have recognizable motifs. One motif is GXGGXXXG, a second motif is $KXEX_6SXKX_{5-6}M$, and a third motif is PXNPTG (Suyama et al., *Protein Engineering* 8:1075-1080 (1995)).

A macromolecule family can be selected based on a conserved and recognizable structural motif such as a primary sequence motif, tertiary structure motif, or both. Members of a macromolecule family can also be recognized based on similar function. For example, a protein family can be identified based on the ability of its members to bind a natural common ligand that is already known. For example, it is known that dehydrogenases bind to dinucleotides such as NAD or NADP. Therefore, NAD or NADP are natural common ligands to a number of dehydrogenase family members. Similarly, kinases bind ATP, which is therefore a natural common ligand to kinases. Other natural common ligands of a macromolecule family can be the coenzymes and cofactors described above.

After a target macromolecule is selected, the selected macromolecule or a functional fragment thereof can be isolated for use in the methods. A functional fragment of a macromolecule is a fragment that is capable of binding at least one ligand that is bound by the full length macromolecule. The macromolecule or fragment can be isolated from a native tissue or organism, from a population of cells maintained in culture, or from a recombinant organism or cell culture. Methods for isolating a protein are known in the art and are described, for example, in Scopes, *Protein Purification: Principles and Practice*, 3$^{rd}$ Ed., Springer-Verlag, N.Y. (1994); Duetscher, *Methods in Enzymology*, Vol 182, Academic Press, San Diego (1990); and Coligan et al., *Current protocols in Protein Science*, John Wiley and Sons, Baltimore, Md. (2000).

A target macromolecule can be cloned and expressed in a recombinant organism using methods that are known to those skilled in the art including, for example, polymerase chain reaction (PCR) and other molecular biology techniques (Dieffenbach and Dveksler, eds., *PCR Primer: A Laboratory Manual*, Cold Spring Harbor Laboratory Press, Plainview, N.Y. (1995); Sambrook et al., *Molecular Cloning: A Laboratory Manual*, 2nd ed., Cold Spring Harbor Laboratory Press, Plainview, N.Y. (1989); Ausubel et al., *Current Protocols in Molecular Biology*, Vols. 1-3, John Wiley & Sons (1998)). The gene or cDNA encoding the target macromolecule is cloned into an appropriate expression vector for expression in an organism such as bacteria, insect cells, yeast or mammalian cells.

Appropriate expression vectors include those that are replicable in eukaryotic cells and/or prokaryotic cells and can remain episomal or be integrated into the host cell genome. Suitable vectors for expression in prokaryotic or eukaryotic cells are well known to those skilled in the art as described, for example, in Ausubel et al., supra. Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like. A vector useful in the methods of the invention can include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are known in the art. One skilled in the art will know or can readily determine an appropriate promoter for expression in a particular host cell.

If desired, a target protein can be expressed as a fusion with an affinity tag that facilitates purification of the target protein. For example, the target protein can be expressed as a fusion with a poly-His tag, which can be purified by metal chelate chromatography. Other useful affinity purification tags which can be expressed as fusions with the target protein and used to affinity purify the protein include, for example, a biotin, polyhistidine tag (Qiagen; Chatsworth, Calif.), antibody epitope such as the flag peptide (Sigma; St Louis, Mo.), glutathione-S-transferase (Amersham Pharmacia; Piscataway, N.J.), cellulose binding domain (Novagen; Madison, Wis.), calmodulin (Stratagene; San Diego, Calif.), staphylococcus protein A (Pharmacia; Uppsala, Sweden), maltose binding protein (New England BioLabs; Beverley, Mass.) or strep-tag (Genosys; Woodlands, Tex.) or minor modifications thereof.

A target macromolecule can be validated as a representative member of a macromolecule family. In some cases, the target macromolecule is well characterized with respect to its binding properties to a natural common ligand. However, if the target macromolecule is encoded by a new, relatively uncharacterized gene, the expressed target macromolecule can be tested to confirm that it binds the natural common ligand. Other common ligands of related macromolecule families, for example, other nucleotide binding macromolecules, or known ligand mimics can also be tested for binding to the target macromolecule.

A target macromolecule can be further validated as a useful therapeutic target by determining if the selected target macromolecule is known to be required for normal growth, viability or infectivity of the target organism or cell. If it is unknown whether the target macromolecule is required for normal growth, viability, or infectivity, the target macromolecule can be specifically inactivated by gene knockout, in a model organism to determine if the macromolecule performs a critical function required for survival or infectivity of the organism or cell. Such a macromolecule providing a critical function is a good target for developing therapeutic agents.

Methods for disrupting a gene to generate a knockout are well known in the art (Ausubel et al., *Current Protocols in Molecular Biology, Vols* 1-3, John Wiley & Sons (1998)). For example, transposable elements can be used to knockout a gene and test for the effect of the knockout on cell growth, viability or infectivity (Benson and Goldman, *J. Bacteriol.* 174:1673-1681 (1992); Hughes and Roth, *Genetics* 119:9-12 (1988); and Elliot and Roth, *Mol. Gen. Genet.* 213:332-338 (1988)). Methods for gene knockouts in protozoa have also been previously described (Wang, *Parasitology* 114:531-544 (1997); and Li et al, *Mol. Biochem. Parasitol.* 78:227-236 (1996)).

Although use of the methods of the invention is exemplified herein with regard to proteins, it is understood that a method of the invention can be used for any other macromolecule that is capable of binding two or more ligands in proximity. Other macromolecules include, for example, biological polymers such as polysaccharides or polynucleotides or synthetic polymers such as plastics and mimics of biological polymers. A polynucleotide can be, for example, a ribozyme, ribosomal RNA or other RNA that is capable of binding a ligand such as a nucleotide.

A method of the invention can include a step of identifying a common ligand. In some cases, a common ligand to a macromolecule family is already known. For example, NAD is a natural common ligand for dehydrogenases, and ATP is a natural common ligand for kinases. However, natural common ligands such as the coenzymes and cofactors often have limitations regarding their usefulness as a starting compound. Substrates and cofactors often undergo a chemical reaction, for example, transfer of a group to another substrate or reduction or oxidation during the enzymatic reaction. However, it is desirable that a ligand to be used as a drug is not metabolizable. Therefore, a natural common ligand or a derivative thereof that is non-metabalizable is generally preferred as a common ligand. Examples of mimetics to the common ligand NADH, for example cibacron blue, are described in *Dye-Ligand Chromatography*, Amicon Corp., Lexington Mass. (1980). Numerous other examples of NADH-mimics, including useful modifications to obtain such mimics, are described in Everse et al. (eds.), *The Pyridine Nucleotide Coenzymes*, Academic Press, New York N.Y. (1982).

A ligand that binds a macromolecule can be identified or characterized using a binding assay including, for example, an equilibrium binding analysis, competition assay, or kinetic assay as described in Segel, *Enzyme Kinetics* John Wiley and Sons, New York (1975), and Kyte, *Mechanism in Protein Chemistry* Garland Pub. (1995). A common ligand can be identified by a competitive binding assay. For example, a macromolecule can be incubated in the presence of a known common ligand and a candidate common ligand, and the rate or extent to which the common ligand binds the macromolecule can be determined. Competitive binding between the common ligand and candidate ligand can be identified from a reduction in the rate or extent of binding of the common ligand to the macromolecule in the presence of the candidate ligand, compared to in the absence of the candidate ligand (see, for example, Segel, *Enzyme Kinetics* John Wiley and Sons, New York (1975)). A candidate ligand that competes with the known common ligand for binding to the common ligand site on the macromolecule is identified as a new common ligand.

Alternatively, absence of competitive binding of a ligand for the site on a protein to which a common ligand binds can be used to determine that a ligand binds to a different location on the protein from the common ligand such as a site that is external to the common ligand binding site. A site that is external to the common ligand binding site on a protein can be, for example, a specificity ligand binding site. Binding at a specificity ligand binding site can be determined by competitive binding with a specificity ligand or mimic thereof. Even if the location where a ligand binds is not known, a determination that the ligand binds to a different location of a protein compared to a second ligand combined with information regarding proximity of the two ligands can be used to map the protein binding site, as demonstrated in Example III. A ligand site on a protein that is identified as external to a common ligand binding site provides a specificity target for which a binding compound can be designed. Such a binding compound designed to interact with the external site will typically show selective binding to the protein compared to other proteins that bind the same common ligand.

In some cases, a common ligand has an intrinsic property that is useful for detecting whether it is bound. For example, the natural common ligand for dehydrogenases, NAD, has intrinsic fluorescence. Therefore, increased fluorescence in the presence of candidate common ligands due to displacement of NAD can be used to detect competition for binding of NAD to a target NAD binding macromolecule (Li and Lin, *Eur. J. Biochem.* 235:180-186 (1996); and Ambroziak and Pietruszko, *Biochemistry* 28:5367-5373 (1989)).

In other cases, when the common ligand does not have an intrinsic property useful for detecting ligand binding, it can be labeled with a detectable moiety. For example, the natural common ligand for kinases, ATP, can be radiolabeled with $^{32}$P, and the displacement of radioactive ATP from an ATP binding protein in the presence of a candidate ligand can be used to identify the candidate as a common ligand. Any detectable moiety, for example a radioactive or fluorescent label, can be added to a ligand so long as the labeled ligand can bind to its binding site on a macromolecule.

A library of candidate ligands can be screened to identify a ligand that binds to a macromolecule, for example, at a common ligand site. Thus, a method of the invention can include assaying a population of candidate first ligands for the ability to bind to a target macromolecule and identifying from the population of candidate first ligands a first ligand that binds to the macromolecule. A first ligand identified from such a screen can then be used to form a complex with the macromolecule and a second ligand that binds proximal to the first ligand can be identified. The screen can be performed by a competitive binding assay on a sample containing the macromolecule, a candidate first ligand and a known common ligand such that a first ligand can be identified as a common ligand by its ability to displace the known common ligand.

A library of candidate ligands can contain a broad range of compounds of various structures. However, the library of candidate ligands can also be focused on compounds that are more likely to bind to a particular site in a macromolecule. A focused library can be designed, for example, to have members that are structural homologs of a natural common ligand or that contain moieties found in the common ligand. A library of candidate common ligands can also be chosen to include members having structural features that are commonly found in a particular class of ligands including, for example, a MOTIF library as described in Example II. The library of candidate common ligands can be a group of analogs or mimetics of the natural common ligand.

One approach to identify a common ligand from a library of candidate ligands is to perform high throughput screening on a large library of molecules. The molecules can be obtained from an existing source such as a commercial or proprietary library or can be synthesized using a combinatorial synthetic method. The iterative approach to combinatorial synthesis is well-known in the art and is set forth, in general, in Houghten et al., *Nature*, 354, 84-86 (1991); and Dooley et al., *Science*, 266, 2019-2022 (1994). In the iterative approach, for example, sublibraries of a molecule having three variable groups are made wherein the first variable is defined. Each of the compounds with the defined variable group is reacted with all of the other possibilities at the other two variable groups. These sub-libraries are each tested for binding to the target macromolecule to define the identity of the second variable in the sub-library having the highest affinity. A new sub-library with the first two variable positions defined is reacted again with all the other possibilities at the remaining undefined variable position. As before, the identity of the third variable position in the sub-library having the highest activity is determined with a binding assay using the target macromolecule. If more variables exist, this process is repeated for all variables, yielding the compound with each variable contributing to the desired binding affinity in the screening process. Promising compounds from this process can then be synthesized on larger scale in traditional single-compound synthetic methods for further biological investigation.

The positional-scanning approach has been described for various organic libraries and for various peptide libraries (see, for example, R. Houghten et al. PCT/US91/08694 and U.S. Pat. No. 5,556,762). In the positional scanning approach, sublibraries are made defining only one variable with each set of sublibraries and all possible sublibraires with each single variable defined (and all other possibilities at all of the other variable positions) are made and tested. For example, one skilled in the art could synthesize libraries wherein 2 fixed positions are defined at a time. From the testing of each single-variable defined library for binding to the target macromolecule, the optimum substituent at that position is determined, pointing to the optimum or at least a series of compounds having a maximum affinity. Thus, the number of sublibraries for compounds with a single position defined will be the number of different substituents desired at that position, and the number of all the compounds in each sublibrary will be the product of the number of substituents at each of the other variables.

Once a library of candidate common ligands is selected, the library is screened, for example, by competition with a natural common ligand for binding to a target macromolecule, to identify at least one common ligand in the library that binds to a conserved site in the target macromolecule. A common ligand identified by the screen is then further characterized with respect to affinity for the target macromolecule. In some cases it is desirable to identify a common ligand that is not a high affinity ligand. Since the common ligand binds to multiple members of a macromolecule family, a high affinity common ligand would likely bind to other members of the family in addition to the target macromolecule. It can therefore be desirable in such cases to identify a common ligand having modest affinity, preferably at or below the affinity of the natural common ligand that binds to the same conserved site. Such a common ligand having modest affinity is then used as a starting compound for identifying a binding compound. Generally, a modest affinity ligand will have affinity for a macromolecule with an equilibrium dissociation constant of about $10^{-2}$ to $10^{-7}$ M, or about $10^{-3}$ to $10^{-6}$ M. The equilibrium dissociation constant of a common ligand or other ligand for a target macromolecule can be greater than $1 \times 10^{-6}$ M.

Another approach to identify a common ligand is to use the three-dimensional structure of a natural common ligand and search a database of commercially available molecules such as the Available Chemicals Directory (MDL Information Systems, Inc.; San Leandro Calif.) to identify candidate common ligands having similar shape or electrochemical properties of the natural common ligand. Methods for identifying similar molecules are well known in the art and are commercially available (Doucet and Weber, in *Computer-Aided Molecular Design: Theory and Applications*, Academic Press, San Diego Calif. (1996); software is available from Molecular Simulations, Inc., San Diego Calif.). A database can be searched, for example, by querying based on chemical property information or on structural information. In the latter approach, an algorithm based on finding a match to a template can be used as described, for example, in Martin, "Database Searching in Drug Design," *J. Med. Chem.* 35:2145-2154 (1992).

Furthermore, if structural information is available for the conserved site in the macromolecule, particularly with a known ligand bound, compounds that fit the conserved site can be identified through computational methods (Blundell, *Nature* 384 Supp:23-26 (1996)). Using such an approach a common ligand can be identified by obtaining a structure model for the binding site of the macromolecule and docking a structure model of a candidate ligand with the structure model of the binding site. Algorithms available in the art for fitting a ligand structure to a protein binding site include, for example, DOCK (Kuntz et al., *J. Mol. Biol.* 161:269-288 (1982)) and INSIGHT98 (Molecular Simulations Inc., San Diego, Calif.).

A molecular structure can be conveniently stored in a computer readable medium and manipulated in a computer system using structural coordinates. Structural coordinates can occur in any format known in the art so long as the format can provide an accurate reproduction of the observed structure. For example, crystal coordinates can occur in a variety of file types such as .fin, .df, .phs, or .pdb as described for example in McRee et al., *Practical Protein Crystallography*, Academic Press, San Diego 1993. Although the examples above describe structural coordinates derived from X-ray crystallographic analysis, one skilled in the art will recognize that structural coordinates can be in any format derived from or used in a method known in the art for determining molecular structure.

A ligand that binds to a target protein can be identified using nuclear magnetic resonance methods. For example, ligand binding can be characterized qualitatively or quantitatively by measuring cross-saturation between the ligand and macromolecule when bound in a complex. An example of a cross-saturation method is WaterLOGSY in which selective water excitation is followed by NOE mixing such that magnetization is effectively transferred via the protein-ligand complex to the free ligand in a selective manner. Under these conditions the resonance of non-bound molecules have an opposite sign and tend to be weaker than the resonances for bound ligands. The macromolecule resonances can be suppressed with a double spin echo scheme, which also suppresses water, and for small and medium sized proteins, where double spin echo may not sufficiently suppress protein sequences, a $T_{1\rho}$ filter can be introduced into the pulse sequence prior to the acquisition period. Thus, the resonances for bound ligands can be readily resolved from unbound molecules and the target macromolecule. Accordingly, WaterLOGSY can be used to screen mixtures of potential ligands to identify those that bind to a target macromolecule, for example, in a screening format. WaterLOGSY is described in further detail in Dalvit et al., *J. Biomol. NMR* 21:349-359 (2001). Nuclear magnetic resonance can also be used to identify a ligand that binds a macromolecule by observing changes in line widths, relaxation rates or NOE values for a ligand upon binding to a macromolecule, as described, for example, in Ni et al., *Prog. Nucl. Magn. Reson. Spectrosc.* 26:517-606 (1994).

Two ligands that bind simultaneously to a macromolecule and in close proximity to each other can be identified in a method of the invention. One of the ligands can be a common ligand, as set forth above. The second ligand can be any molecule that is capable of binding to the macromolecule in proximity with the first ligand at a site that is external to the common ligand binding site. In the case of an enzyme target, a substrate that is acted upon by a cofactor usually provides a reasonable candidate as a second ligand. In particular, the common ligand site and substrate site are most likely located in physical proximity to each other in an enzyme's three-dimensional structure to facilitate catalysis. In particular, the three-dimensional geometric relationship between the common ligand site and substrate ligand sites has been shown to be conserved in evolutionarily related dehydrogenases (Sem and Kasper, *Biochemistry* 31:3391-3398 (1992)). Although the relationship between the sites is conserved, the substrate site itself imparts molecular properties that distinguish the protein from other proteins in the same protein family. Thus, the substrate site is referred to as a "specificity site." The specificity site of a macromolecule provides a binding site for a ligand that selectively associates with the macromolecule compared to other macromolecules that are in the same common ligand-binding family. A site that is external to a common ligand binding site such as a substrate specificity site can be exploited as a potential binding site for the identification of a ligand that has specificity for one macromolecule over another member of the same macromolecule family. A site that is external to a common ligand binding site such as a specificity site is distinct from the common ligand binding site in that the natural common ligand does not bind to the specificity site.

A second ligand such as a specificity ligand can be identified using the above-described methods including, for example, a binding assay, a structural characterization or database search. In the case where one or both ligands are known to bind to a macromolecule, a method of the invention can be used to determine that the two ligands bind in proximity to each other. Furthermore, as set forth below the relative orientation of or distance between the two ligands can be determined and used to design a binding compound or a library of candidate binding compounds.

A method of the invention can also be used in a screening format to identify a second ligand that is capable of binding to a macromolecule simultaneously with a first ligand and in proximity to the first ligand. Thus, a second ligand that has not been previously shown to bind to the macromolecule can be identified as being capable of binding the macromolecule based on detection of an interaction with another ligand. A second ligand can be identified from a library of candidate ligands in a screening method.

Accordingly, the invention provides a method for obtaining a focused library of candidate binding compounds, wherein the members of the protein family bind a common ligand. The method includes the steps of (a) providing a plurality of samples containing the protein and a first ligand under conditions wherein the first ligand and the protein form a bound complex, wherein the protein is a member of a family of proteins that bind a common ligand; (b) assaying a population of candidate second ligands for the ability to transfer magnetization to the first ligand in a sample from the plurality; (c) identifying, from the population of candidate second ligands, a second ligand that transfers magnetization to the first ligand, thereby determining that the two ligands are proximal to each other in a ternary bound complex with the protein; (d) observing competitive binding between one of the two ligands and the common ligand, thereby determining that the competitive binding ligand binds to the common ligand binding site of the protein; and (e) obtaining a population of candidate binding compounds including the competitive binding ligand, or a fragment thereof, linked to one of a plurality of homologs of the other ligand, whereby the population of candidate binding compounds contains binding compounds that bind to members of the protein family.

A library of second ligands can be obtained as set forth above. In the case of an enzyme target, the library can be designed based on the structure of a natural specificity ligand since a substrate that is acted upon by a cofactor is proximal to a common ligand, as set forth above. A population of second ligands can also be designed to include members having structural features that are commonly found in a particular class of ligands including, for example, a MOTIF library as described in Example II. A population of second ligands to be used in a method of the invention can be synthesized using combinatorial methods similar to those set forth above.

Thus, ligands that bind proximal to each other in a complex with a macromolecule can be identified by screening a library of candidate first ligands and a library of candidate second ligands. Accordingly, a method of the invention can include the steps of: (a) providing a protein that is a member of a family of proteins that bind a common ligand; (b) assaying a population of candidate first ligands for the ability to bind the protein; (c) identifying from the population of candidate first ligands a first ligand that binds to the protein; (d) providing a plurality of samples containing the protein and the first ligand under conditions wherein the first ligand and the protein form a bound complex; (e) assaying a population of candidate second ligands for the ability to transfer magnetization to the first ligand in a sample from the plurality; (f) identifying, from the population of candidate second ligands, a second ligand that transfers magnetization to the first ligand, thereby determining that the two ligands are proximal to each other in a ternary bound complex with the protein; (g) observing competitive binding between one of the two ligands and the common ligand, thereby determining that the competitive binding ligand binds to the common ligand binding site of the protein; and (h) obtaining a population of candidate binding compounds including the competitive binding ligand, or a fragment thereof, linked to one of a plurality of homologs of the other ligand, whereby the population of candidate binding compounds contains binding compounds that bind to members of the protein family.

An advantage of designing a bi-ligand binding compound based on screening candidate ligand libraries is that the number of bi-ligand compounds that need to be synthesized and tested compared with a classic structure activity relationship (SAR) approach is reduced. For example, two libraries of 1000 ligands can be rapidly screened to identify a small number of ligands that bind a macromolecule. Pairs of identified ligands can then be combinatorially assayed for the ability to simultaneously bind the macromolecule. If two ligands are found to simultaneously bind the macromolecule, proximal atoms on each ligand can be determined to guide chemistry to link the two ligands, with a small number of different linkers, for example, 5. Thus, only 5 compounds need to be synthesized. In contrast, a more traditional SAR approach would be to synthesize all possible pairs, resulting in a library of about $1000 \times 1000 \times 5 = $ million compounds.

Two ligands that bind simultaneously to a macromolecule and in close proximity to each other can be identified in a method of the invention by detecting magnetization transfer between the two ligands when bound in a ternary complex with the macromolecule. For example, as demonstrated in Example I, interactions between proximal ligands can be identified based on NOE crosspeaks observed in a 2D ($^1$H, $^1$H) NOESY spectrum. In the case of a ($^1$H, $^1$H) NOESY spectrum obtained for ligands in a ternary complex with a macromolecule, observation of cross peaks occurring at the chemical shift positions of the atoms from separate ligands indicate that the atoms are proximal. Such inter-ligand NOE peaks can be resolved from intra-ligand NOE signals by adjusting the mixing time in the NOESY pulse sequence. Because the strength of an NOE interaction between two protons is dependent on $1/r^6$, where r is the distance between the two protons, and because most inter-ligand proximal protons will be further apart than intra-ligand proximal protons, the mixing time can be increased to allow selective detection of inter-ligand NOE peaks compared to most intra-ligand and intra-protein NOE peaks.

Typically magnetization transfer between proximal ligands is observed in a sample having a molar excess of ligands compared to the protein to which they bind. Because the lifetime of an alteration to a nucleus due to a magnetization transfer, such as an NOE interaction, is usually longer than the residence time for ligands in a complex with a protein, the number of ligand nuclei for which magnetization transfer is observed exceeds the number of protein molecules in the sample. Thus, the protein acts to turn over altered ligands to amplify the observed signal in a condition where the ligand is in excess. The amplified signals can be readily distinguished from signals arising from the protein.

In cases where ligand is not in excess over the protein, a signal that arises from a ligand atom can be identified using known methods for assigning resonances. Such signals can be differentiated from signals arising from other atoms in a sample using isotope enrichment. For example, where protons of a ligand are to be observed the protein to which the ligand binds can be labeled with deuterium ($^2H$) to remove signals arising from the protein. A ligand enriched with an NMR detectable isotope at an observed atom position can be used to enhance detection of a signal arising from the ligand atom. In addition, a signal can be selectively detected when an isotope filter or relaxation filter is used such as any of those described in Cavanaugh et al., *Protein NMR Spectroscopy: Principles and Practice*, ch. 7, Academic Press, San Diego Calif. (1996).

A protein can be isotopically labeled with $^2H$ atoms to simplify spectra by replacing NMR-visible $^1H$ atoms. For example, $^2H$ atoms can be incorporated at both exchangeable and non-exchangeable positions in a macromolecule by growing an organism expressing the macromolecule in the presence of $D_2O$ ($^2H_2O$). $^2H$ atoms can be incorporated or maintained at exchangeable positions, such as at amides or hydroxyls of a protein, by carrying out steps in the isolation of the macromolecule in deuterated solvent. For protein labeling, acetate or glucose can be provided as the sole carbon source in the presence of $D_2O$ if complete deuteration on carbon is desired. If pyruvate is used as the sole carbon source, there will be protons only on the methyl groups of Ala, Val, Leu and Ile (Kay, *Biochem. Cell Biol*. 75:1-15 (1997).

When NOE methods are used to identify proximal ligands, the measurements can be performed at low temperature to increase NOE build-up rates and therefore enable the observation of inter-ligand NOES at shorter mixing time. As temperature decreases, mixing time can be decreased resulting in ($^1H$, $^1H$) NOESY spectra with increased sensitivity, thereby allowing observation of peaks that are not visible or that are difficult to distinguish at higher temperatures. Furthermore, measurement of inter-ligand NOES at shorter mixing times and lower temperature also decreases spin-diffusion and protein mediated magnetization transfer which often have deleterious effects on the intensity of NOE signals. In general, higher sensitivity NOE measurements can be obtained at temperatures below 10° C. Thus, a method of the invention can include detecting magnetization transfer at temperatures below 80° C., below 5° C. or below 20° C., so long as the sample is in a liquid state.

Further, two ligands that bind simultaneously to a macromolecule and in close proximity to each other can be identified in a method of the invention by detecting magnetization transfer between the two ligands when bound simultaneously with the macromolecule. For example, interactions between proximal ligands can be identified based on measuring cross-saturation between the ligands when bound in a complex with the macromolecule. A saturation transfer difference (STD) method can be applied in which selective excitation of a particular resonance of one ligand is followed by polarization transfer such that magnetization is effectively transferred, in a selective manner to a proximal ligand when bound in a complex. Under these conditions the resonances of non-bound molecules have an opposite sign and tend to be weaker than the resonances for bound ligands. Accordingly, STD between ligands can be used to screen individual compounds or mixtures of potential ligand to identify those that bind to a target macromolecule. The cross saturation achieved via inter-ligand magnetization transfer can be achieved with natural abundance of NMR-visible isotopes. However, it can be advantageous to use deuterium labeled protein to effectively remove the effects of the proton mediated magnetization transfer from the protein. The STD method is particularly useful for use in a screening format because the NMR signals that are used for identifying proximal ligands can be collected on a relatively short time frame compared to other methods of determining ligand binding. In addition to providing a functional identification that the ligand binds to the protein, the STD method when used to identify proximal ligands provides structural information regarding the relative location of ligands when bound to the protein.

Because the proximity of ligands is determined based on detection of interactions between ligands and does not require detection of interactions with the macromolecule to which they are bound, isotopically labeled macromolecules are not necessary. Thus, a macromolecule used in a method of the invention can contain a natural abundance of NMR-visible isotopes for the atoms it contains. Examples of NMR-visible isotopes are $^1H$ which is present in a natural abundance of 99.98%, $^{13}C$ which is present in a natural abundance of 1.11% and $^{15}N$ which is present in a natural abundance of 0.37%. A macromolecule can contain at most about 1% of the non-NMR-visible hydrogen isotope $^2H$, at most 1.5% of $^{13}C$ or at most about 0.5% of $^{15}N$.

Although labeled macromolecules are not required, a labeled macromolecule can be used in a method of the invention. For example, once proximal ligands are identified, the orientation of one or more ligands can be confirmed or further investigated by identifying NMR interactions with a labeled macromolecule. In applications where labeling of a macromolecule is desired in order to further investigate the orientation of one or more ligand when bound to the macromolecule or to investigate structural properties of the macromolecule binding site, strategies and methods known in the art for introducing one or more isotopic label can be used (see, for example, Laroche, et al., *Biotechnology* 12:1119-1124 (1994); LeMaster *Methods Enzymol*. 177:23-43 (1989); Muchmore et al., *Methods Enzymol*. 177:44-73 (1989); Reilly and Fairbrother, *J. Biomolecular NMR* 4:459-462 (1994); Ventors et al., *J. Biomol. NMR* 5:339-344 (1995); and Yamazaki et al., *J. Am. Chem. Soc*. 116:11655-11666 (1994)).

A method of the invention is well suited for use with large macromolecules because proximal ligands in a complex with a macromolecule can be identified absent knowledge of the structure of the macromolecule or assignment of resonances for atoms of the macromolecule. In particular, large macromolecules having a monomeric molecular weight greater than 20 kDa, which often are not completely NMR assigned, or for which complete structure models are not available, can be characterized with respect to pairs of ligands that bind thereto. Because observation of magnetization transfer between ligands can be enhanced when the ligands experience low rotational mobility, macromolecules having monomeric molecular weights greater than 25 kDa, 30 kDA, 40 kDa, 50 kDa, 75 kDa, 100 kDa or 150 kDa can be used. Furthermore, a method of the invention can be used to identify proximal ligands for other macromolecules with low rotational mobility such as membrane bound proteins or multimeric proteins having at least 2, at least 3, or at least 4 monomers, wherein the monomers can have monomeric molecular weights in the range described above.

Because structural analysis of the macromolecule itself is not required to identify or characterize proximal ligands in a method of the invention, a macromolecule can be used for which resonance assignments have not been made for a majority of the atoms in the macromolecule. Thus, a method of the invention can use a macromolecule for which less than 90%, 80%, 70%, 60%, 50%, 40%, 30%, 20% or 10% of the atoms have been assigned a resonance.

Proximal ligands are identified in the methods under conditions where a majority of the macromolecule is bound in a complex with two ligands. A condition in which a majority of the macromolecule is bound in a complex with two ligands can be achieved when the macromolecule is present at relatively low concentrations and excess ligand is present. Thus, although a method of the invention can be performed with millimolar concentrations of a macromolecule, as is often required for structure determination by NMR, lower concentrations such as concentrations below 200 micromolar can be used. The use of low concentrations of a macromolecule is advantageous when the target macromolecule is available in limited supplies or where screening procedures require a large number of samples containing the macromolecule. In such cases, concentrations of the macromolecule below 100 micromolar, 50 micromolar, 40 micromolar, 25 micromolar, or 10 micromolar can be used.

Ligands can be added to a macromolecule-containing sample in molar excess such that a majority of the macromolecule in the sample will be bound in a complex with the ligands. The extent of the molar excess can be determined using known methods for determining percent occupancy based on equilibrium binding equations, a known or predicted affinity constant of a ligand for a macromolecule and the concentration of the macromolecule in a sample (see, for example, Segel, supra). Alternatively, excess ligands can be added and the amount sufficient to result in a majority of the macromolecule being bound to the ligands, can be determined empirically, for example, by titration.

Proximal ligands are identified in the methods under conditions where the ligands bound in a complex with the macromolecule are inert to catalysis by the macromolecule. In cases where the macromolecule is a catalyst, a ligand mimic can be chosen that does not undergo catalysis or that undergoes catalysis at a rate that is slow compared to the timeframe in which ligand interactions are measured. In cases where a reactive ligand is used with an enzyme, conversion of the ligand to a product can be prevented by altering conditions such that catalytic activity of the enzyme is inhibited. For example, anaerobic conditions can be employed to inhibit reactions requiring oxygen, pH can be adjusted to inhibit reactions requiring a particular protonation state of a catalytic residue, or a noncompetitive inhibitor can be added.

Once a pair of proximal protons from separate ligands is identified for a particular ternary complex, the distance between the ligands can be estimated. In particular, an atom of a first ligand that is proximal to an atom of a second ligand in a ternary complex can be identified. For example, the distance between the ligands can be estimated based on the distance separating the proximal protons as determined by measurements of NOE build-up rates using methods described in Cavanaugh et al., supra (1996).

The distance determined to separate the proximal protons can then be used in combination with the average bond lengths separating other ligand atoms from the protons to estimate inter-ligand atomic distance in the ternary complex. For example, the distance between the atoms from each ligand that are directly bonded to the proximal protons can be estimated from the sum of the NOE measured distance and the theoretical lengths of both atom-proton bonds. Similarly, by summing the bond lengths separating other atoms from the proximal protons and considering bond angles, the distance separating these other atoms can be estimated. Even when distances are not measured, two ligands can be identified as proximal based on observation of magnetic interactions, when spin diffusion is absent or otherwise accounted for.

Spin diffusion can be eliminated using QUIET NOESY (Quenching Undesirable Indirect External Trouble in NOESY, Neuhaus et al. "The Nuclear Overhauser Effect in Structural and Conformational Analysis", Wiley-VCH, New York, 2000) or NOE build-up curves. QUIET NOESY measurements can be performed to avoid artificial NOE cross-peaks arising from spin diffusion. These measurements differ from a conventional NOESY measurements by the presence in the middle of the mixing time of a selective (or a combination of selective) 180 degree pulse(s) to invert only the signals of the two protons for which the length of separation is to be determined. NOE build-up curves can be used to plot NOE vs. mixing time such that signals due to direct NOE transfer can be differentiated from those that are indirect or due to spin diffusion based on the shapes of the curves as described, for example, in Cavanaugh et al., supra (1996).

Those skilled in the art will understand that depending upon the degree of conformational freedom for the ligands in an observed ternary complex and the number of observed inter-ligand interactions, the estimation of distances between atoms that are increasingly removed from the proximal ligands can have different levels of precision. For example, in the case of two proximal aromatic ring structures for which two pairs of interactions are observed, the relative orientations of the rings can be estimated with relatively high precision and the distance separating any of the atoms in the two ring system can be determined with a relatively high level of confidence due to two-point anchoring between the planar rings. As set forth below, the estimated distance separating two ligands can be used to guide the selection of a linker to attach the proximal ligands in designing a bi-ligand binding compound. Depending upon the level of confidence with which the distance is determined, the variety of linker types and ligand attachment points represented in a library of potential binding compounds can be adjusted.

A ligand-probe having an attached antenna moiety can be used in a method of the invention. An antenna moiety provides an NMR-detectable nucleus that can occupy a position away from the ligand moiety of the ligand-probe such that a magnetic interaction between the nucleus and a proximal ligand can be used to identify the relative location of the proximal ligand even if it is too distant to magnetically interact with the ligand moiety of the ligand-probe. Thus, an antenna moiety can extend the range within which proximal ligands can be identified.

Accordingly, the invention provides a method for obtaining a focused library of candidate binding compounds for a protein family, wherein the members of the protein family bind a common ligand. The method includes the steps of: (a) providing a ligand-probe having an antenna moiety, wherein the ligand-probe binds to the common ligand binding site of a protein, wherein the protein is a member of the protein family; (b) providing a sample containing the protein, the ligand-probe and a second ligand under conditions wherein the ligand-probe, the second ligand and the protein form a bound complex; (c) detecting magnetization transfer between the antenna moiety of the ligand-probe and the second ligand in the bound complex, thereby determining that the antenna moiety and second ligand are proximal in the bound complex; and (d) obtaining a population of candidate binding compounds comprising the ligand-probe, or a fragment thereof, linked to one of a plurality of second ligand homologs, whereby the population contains binding compounds that bind to members of the protein family.

Also provided is a method for obtaining a focused library of candidate binding compounds, wherein the members of the protein family bind a common ligand. The method includes the steps of: (a) providing a ligand-probe having an antenna moiety, wherein the ligand-probe binds to the common ligand binding site of a protein, wherein the protein is a member of the protein family; (b) providing a plurality of samples containing the protein and the ligand-probe under conditions wherein the ligand-probe and the protein form a bound complex, wherein the protein is a member of a family of proteins that bind a common ligand; (c) assaying a population of candidate second ligands for the ability to transfer magnetization to the antenna moiety of the ligand-probe in a sample from the plurality; (d) identifying, from the population of candidate second ligands, a second ligand that transfers magnetization to the antenna moiety of the ligand-probe, thereby determining that the two ligands are proximal to each other in a ternary bound complex with the protein; and (e) obtaining a population of candidate binding compounds comprising the ligand-probe, or a fragment thereof, linked to one of a plurality of homologs of the other ligand, whereby the population of candidate binding compounds contains binding compounds that bind to members of the protein family.

Based on the length of an antenna moiety and its point of attachment to a ligand moiety, the relative location of a proximal ligand can be determined. Depending on where the antenna moiety is attached in the ligand-probe, the direction and approximate location of the other proximal ligand relative to the ligand moiety can be determined. Because the ligands are bound at a particular orientation in their respective binding sites, an antenna moiety can provide information regarding the relative structural relationships of proximal binding sites.

An antenna moiety can have any of a variety of structures that extend from a ligand moiety including, for example, those described below with respect to linkers, so long as an NMR-observable nucleus is included. An antenna moiety can have a structure that is selected based on a particular distance desired for separating an NMR-observable nucleus and the ligand moiety to which it is attached or based on a particular orientation for the NMR-observable nucleus relative to the ligand moiety. The relative distance and orientation can be determined based on visual inspection of a structure model for the protein to be tested or of a homolog of the protein. The distance and orientation can also be empirically determined, for example, by iteration of a method of the invention where the composition of the antenna moiety is altered until a desired or diagnostic interaction is observed.

An antenna moiety can have a structure that is selected based on magnetic properties to be observed. For example, an antenna moiety can contain an NMR-observable nucleus that is magnetically isolated from other atoms in the ligand probe to facilitate or improve a particular NMR measurement. As demonstrated in Example IV use of an ether linkage favored observation of direct NOE interactions between a terminal methyl and a proximal ligand at short mixing times compared to indirect NOE interactions due to magnetization transfer in the ligand probe. The ether linkage further provided an environment for the terminal methyl protons where relaxation effects due to vicinal proton coupling did not occur, thereby providing a stronger signal for the methyl protons. Isolation of an NMR-observable nucleus can also be achieved by providing an adjacent ether oxygen; carbonyl carbon; thioether, sulfone or sulfoxide sulfur; deuterated carbon; selenium; or nitrogen. An NMR-observable nucleus used in an antenna moiety can be at an internal position or at a terminal position. An example of an internal position that is useful is a proton in a phenyl or other aromatic ring structure that is deuterated at the other positions.

An antenna moiety can also have an NMR-observable nucleus that is in an environment that differs from that of other nuclei in the ligand-probe such that the nucleus for which observation is desired can be selectively excited. As demonstrated in Example V, methyl protons at a position terminal to an aliphatic, ether-containing antenna moiety were selectively saturated compared to the aromatic protons of the attached ligand moiety. Those skilled in the art will understand that antenna moieties of different lengths, composition or point of attachment can be routinely tested using a binding assay with the target macromolecule.

A ligand-probe can contain a plurality of antenna moieties, such as 2, 3, 4, 5, or more antenna moieties attached to a ligand moiety, thereby forming a ligand multi-probe. The composition, length and point of attachment for each antenna moiety of a ligand multi-probe can be determined as described above. The antenna moieties included in a ligand multi-probe can be selected such that the nuclei of each antenna that is to be observed will resonate at a frequency that is readily distinguished from the other antenna nuclei that are to be observed. Thus, the nuclei of the antenna moieties can be separated in a single spectrum to facilitate identification of a proximal ligand and determination of its orientation relative to the ligand multi-probe.

Comparison of signals arising from antennas attached at different points in a ligand multi-probe provide information regarding the direction and distance that separates it from one or more proximal ligands. Thus, the ligand multi-probe can be used to determine the direction and approximate location of proximal ligands bound to different sites on the protein. A ligand multi-probe can also be used to determine the orientation of the ligand moiety of the ligand multi-probe relative to the proximal ligand based on the points on the ligand moiety at which each antenna moiety is attached and the atoms of the proximal ligand that the antenna moiety interacts with. Thus, using the methods described below, a linker can be designed to connect the two ligands, or fragments thereof or homologs thereof, such that their relative positions are in accordance with the observed orientations. It is understood that an antenna can be attached to any of a variety of ligands including, for example, a common ligand or specificity ligand.

Once proximal ligands of a macromolecule are identified they can be used to design a binding compound or a library of candidate binding compounds for the macromolecule. A binding compound can contain a moiety formed by a first ligand, fragment of the first ligand or homolog of the first ligand, attached by a linker to any of a second ligand, fragment of the second ligand or homolog of the second ligand. A fragment of a ligand included in a linked binding compound can be any portion of the ligand that interacts with the target protein in such a way as to participate in specific binding. For example, a fragment of a ligand-probe that can be linked in a binding compound can be a ligand moiety, or fragment thereof.

A portion of a ligand that interacts with a protein can be identified according to magnetic interactions of atoms of the particular portion of the ligand with atoms of the protein. Such interactions can be observed using methods known in the art such as those described in WO 99/60404 and U.S. Pat. No. 5,698,401. A portion of a ligand that interacts with a protein can also be identified by visual inspection of a structure model of a complex of the ligand and protein, such as an X-ray crystallographic or NMR structure; docking of a structure model of the ligand to a structure model of the protein; or comparison to other ligands that bind to the protein.

A library of candidate binding compounds can be obtained in which a moiety formed by a first ligand, fragment of the first ligand or homolog of the first ligand is linked to a variety of homologs of the other ligand. Where the library is directed to one or more protein in a common ligand binding family, diversity of the library occurs at the portion of the binding compound that will interact with the specificity ligand binding site (specificity portion), thereby providing specificity for particular members of the family. The common ligand portion of the bi-ligand provides favorable interactions, thereby improving affinity of the binding compound for its target compared to the affinity that would be provided by the specificity portion alone.

Diversity of the library can be further increased by using a variety of linkers or diverse combinations of homologs of both ligands. A homolog or population of homologs can be selected based on structural similarity to a particular ligand. A population of homologs can also be produced by a combinatorial approach in which a core structure of a ligand is modified or in which moieties found in a particular ligand are combined.

A linker is selected based on the ability to provide sufficient length and conformational freedom for the ligands, or homologs thereof, to associate with their respective sites on the macromolecule. A linker can include any number of atoms that can attain a conformation resulting in the desired length between linked moieties including, for example, 1, 2, 3, 4, 5, 6, 7, 8, 9, 10 or more atoms that are linearly connected. Linear connection is used to describe the positions of the atoms relative to each other in a linker and is not intended to limit the linker to a linear structure. Accordingly, a linker can have atoms that form branch structures off of linearly connected atoms or a linker can be formed by one or more cyclic structure.

A linker can be directly attached to a ligand at one of the atoms in the proximal pair. The linker can also be attached to a ligand, or homologs thereof, at the position of one of the atoms in the proximal pair whether or not the same atom occupies the position in the original ligand and in the linked compound. The linker is designed to have at least two positions for attaching at least two ligands, or homologs thereof.

The point of attachment for a linker on each ligand, or homologs thereof, can be chosen to result in a binding compound having the ligands, or homologs thereof, separated by a distance similar to that observed for the ligands in the macromolecule complex. The distance between the two linked portions of a binding compound can be determined based on the positions of the proximal atoms in each portion. The position of one or both atoms can be occupied by another atom that is, for example, present due to the chemistry selected for attachment. The distance between the portions can also be determined based on the positions of other atoms where the relative positions in the bound complex are known.

Those skilled in the art will understand that linkers of different lengths, composition or points of attachment can be routinely tested using a binding assay with the target macromolecule. The number of variations to be tested can be determined, for example, based on the degree of confidence in the distance estimate for the two ligands to be joined. Variations can be individually tested in a binding assay with the target macromolecule or a library of variants can be screened for the ability to bind to the target macromolecule. Thus, a method of the invention can be carried out in an iterative fashion wherein the steps of the method are repeated with linkers of different lengths or compositions until a binding compound having a desired linkage is obtained. Similar iterations can be performed with different linked moieties until a binding compound having a desired affinity or specificity or both is identified.

In another embodiment a common ligand is linked to each of a plurality of homologs or a proximal ligand to create a focused library of candidate binding compounds. The use of a natural common ligand, or mimic thereof, as a partner in a linked bi-ligand can be advantageous because natural common ligands can be more effective in crossing biological membranes such as bacterial or eukaryotic cell membranes. For example, a transport system actively transports the nicotinamide mononucleotide half of the NAD molecule (Zhu et al., *J. Bacteriol.* 173:1311-1320 (1991)). Therefore, it is possible that a bi-ligand comprising a common ligand, or derivative thereof, that is actively transported into a cell will facilitate the transport of the bi-ligand across the membrane.

Linkers that are useful for generating a binding compound include, for example, substituted phosgene, urea, furane and salicylic acid. However, any chemical group with two reactive sites that can be used to position a first ligand and a second ligand in an optimized position for binding to their respective sites can be used as a linker.

Another group of linkers includes molecules containing phosphorous. These phosphorus-containing molecules include, for example, substituted phosphate esters, phosphonates, phosphoramidates and phosphorothioates. The chemistry of substitution of phosphates is well known to those skilled in the art (Emsley and Hall, *The Chemistry of Phosphorous: Environmental, Organic, Inorganic and Spectroscopic Aspects*, Harper & Row, New York (1976); Buchwald et al., *Methods Enzymol.* 87:279-301 (1982); Frey et al., *Methods Enzymol.* 87:213-235 (1982); Khan and Kirby, *J. Chem. Soc. B*:1172-1182 (1970)). A related category of linkers includes phosphinic acids, phosphonamidates and phosphonates, which can function as transition state analogs for cleavage of peptide bonds and esters as described previously (Alexander et al., *J. Am. Chem. Soc.* 112:933-937 (1990)). The phosphorous-containing molecules useful as linkers can have various oxidation states, both higher and lower, which have been well characterized by NMR spectroscopy (Mark et al., *Progress in NMR Spectroscopy* 16:227-489 (1983)).

The reactive groups on a linker and the ligands, or homologs thereof, to be attached should be reactive with each other to generate a covalent attachment of the ligands, or homologs thereof, to the linker at a sufficient distance for binding to their respective binding sites on the macromolecule. A preferred reaction is that of a nucleophile reacting with an electrophile. Many of the above described linkers have electrophilic groups available for attaching ligands. Electrophilic groups useful for attaching ligands include electrophiles such as carbonyls, alkenes, activated esters, acids and alkyl and aryl halides.

The linkers having electrophilic groups are preferably attached to ligands, or homologs thereof, having nucleophilic groups including, for example, alcohols, amines, or mercaptans. However, if a ligand, or homolog thereof, is identified that does not have appropriate reactive groups for attaching a linker, it can be modified to incorporate a reactive group at or near the position of an atom that was identified as one of the proximal atoms. If the ligand, or homolog thereof, cannot be modified to generate an appropriate reactive group in a desired position, an additional screen can be performed, as described above, to identify a homolog having desired binding characteristics as well as a chemical group in the proper position for attachment of a linker.

A compound that binds a protein can be obtained by screening a library of binding compounds for the ability to bind to a target macromolecule and identifying a member of the library that binds to the protein. The screen can be performed using the methods described above for determining binding of a ligand to a macromolecule. The compound can have specificity for a first protein over a second protein. For example, a compound can have specificity for a first protein that binds a common ligand compared to a second ligand that binds the same common ligand. A binding compound obtained by a method of the invention can have specificity for one or more protein of a common-ligand binding family compared to a non-family protein. Such specificity can be due to more favorable interactions of the specificity portion of a compound with the first protein compared to its interactions with the second protein. Specificity can be characterized as at least about 2 fold higher affinity, at least about 3 fold higher affinity, at least about 4 fold higher affinity, at least about 5 fold higher affinity, at least about 10 fold higher affinity, at least about 25 fold higher affinity, at least about 50 fold higher affinity, at least about 100 fold higher affinity or at least about 1000 fold higher affinity.

A binding compound obtained by a method of the invention, by combining moieties from two ligands that bind proximal to each other in a complex with a protein, will have higher affinity or specificity for the protein than the affinity or specificity of either ligand alone. The affinity of a compound, obtained by a methods of the invention, for a protein can have an equilibrium dissociation constant of at most about $10^{-6}$ M, $10^{-8}$ M, $10^{-9}$ M, $10^{-10}$ M, $10^{-11}$ M or $10^{-12}$ M.

Although the methods of the invention have been described above with respect to a complex in which two ligands bind a macromolecule and in which a bivalent binding compound is designed, a method of the invention can also be used to identify 3 or more ligands that are proximal when bound to a macromolecule and to link the ligands using 2 or more linkers in order to form a multi-ligand binding compound. A method of the invention can also be used to design a multi-ligand binding compound by sequentially adding ligands to a binding compound. Thus, a method of the invention can include the steps of (a) obtaining a sample containing a macromolecule, a first ligand and a second ligand under conditions wherein a bound complex is formed containing the first ligand, the second ligand and the macromolecule; (b) detecting magnetization transfer between the first ligand and the second ligand in the bound complex; (c) determining from the magnetization transfer the distance between an atom of the first ligand and an atom of the second ligand in the bound complex; (d) obtaining a binding compound including the first ligand, or a fragment thereof, the second ligand, or a fragment thereof, and a linker, whereby the binding compound is capable of binding the macromolecule; and (e) repeating steps (b) through (d), wherein the first ligand is replaced by the binding compound obtained in step (d) and the second ligand is replaced by another ligand.

Once a binding compound has been obtained its specificity for a particular member of a macromolecule family can be determined by determining the affinity of the compound for the macromolecule compared to other macromolecules in the family. If the compound binds to a first macromolecule with higher affinity or at a faster rate than a second macromolecule it will be identified as being specific for the first macromolecule. Although absence of binding to the second molecule in such an assay is preferable in many situations, any increase in specificity for the first macromolecule over the second can be exploited in applications were specificity is desired. Furthermore, determination that a compound has specificity for one macromolecule over another, even if moderate, can identify the compound as a candidate for iterative improvement in a method of the invention. In particular, the compound so identified can be bound in a complex with the target macromolecule and used to identify a ligand that binds in a proximal location. Covalent linkage of the compound and proximal ligand can yield a subsequent binding compound with higher affinity and improved specificity for the macromolecule compared to other macromolecules in the same family.

The invention further provides a method for identifying a compound having specificity for a particular member of a protein family, compared to other members of the protein family, prior to synthesizing the compound. The method includes the steps of: (a) observing competitive binding of the common ligand and a first ligand to a first protein, (b) observing competitive binding of the common ligand and a first ligand to a second protein, wherein the first and second proteins are members of the protein family, thereby determining that the first ligand binds to the common ligand binding site of the first and second proteins; (c) providing a sample containing the first protein, the first ligand and a second ligand; (d) providing a sample containing the second protein, the first ligand and the second ligand; (e) comparing the degree of magnetization transfer between the first ligand and the second ligand for the samples of parts (b) and (c); and (f) obtaining a binding compound including the first ligand, or a fragment thereof, linked to the second ligand, or a fragment thereof, whereby the binding compound selectively binds the first protein compared to the second protein.

Two or more ligands to be linked, or for which homologs can be identified, in order to produce a binding compound with specificity for a first macromolecule over a second macromolecule can be identified by comparison of magnetization transfer between the ligands when bound to the different macromolecules. Absence of magnetization transfer between ligands in the presence of the second macromolecule will indicate that at least one of the ligands does not bind the second macromolecule or that, if the ligands both bind they are relatively distal from each other. Thus, a binding compound in which the ligands, or homologs thereof, are linked according to distances observed in the first macromolecule will have reduced affinity for the second macromolecule either because one of the ligands, or homologs thereof, does not contribute to a favorable binding interaction or because the ligands, or homologs thereof, are sterically constrained from binding to both sites on the second macromolecule. Similarly, a library of candidate binding compounds will have a higher probability of containing a compound that is specific for the first macromolecule.

A greater degree of magnetization transfer between two ligands when bound to a first macromolecule compared to when bound to a second macromolecule can indicate a shorter distance between the ligands in the first macrolecule. Based on the distance measured between the ligands in both macromolecule complexes the length of a linker can be chosen to favor binding to the first macromolecule by being long enough to allow the two ligands, or homologs thereof, to bind to both sites on the first macromolecule but too short to allow both ligands, or homologs thereof, to bind their respective sites on the second macromolecule.

The following examples are intended to illustrate but not limit the present invention.

Example I

Design of a Potent and Specific Bi-Ligand for p38α MAP Kinase

This Example demonstrates use of the methods of the invention to design a potent and selective inhibitor for activated p38α MAP kinase, starting from relatively weak binding fragments.

A library of 29 PBBA structure analogs was screened against unlabeled p38α MAP kinase (p38α) as follows. Samples containing 10 to 30 micromolar concentration of unactivated p38α MAP kinase and 0.1 to 1.0 millimolar concentration of one of the PBBA structure analogs were obtained. The samples were screened using WaterLOGSY with saturations times of 2 s (frequency selective excitation via a train of 232 6 ms π pulses with a GAUSS profile at an 80 Hz RF field strength) with solvent suspension using WATER-GATE at 4° C. WaterLOGSY is further described in Dalvit et al. *J. Biomol. NMR* 21:349-59 (2001) Dalvit et al. *J. Magn. Res.* B112:282-288 (1996) and Dalvit et al., *J. Biomol. NMR* 11:437-444 (1998). Among the compounds screened, p-butyl benzoic acid (PBBA) showed cross-saturation effects with p38α indicating binding to the protein.

Figure 2:
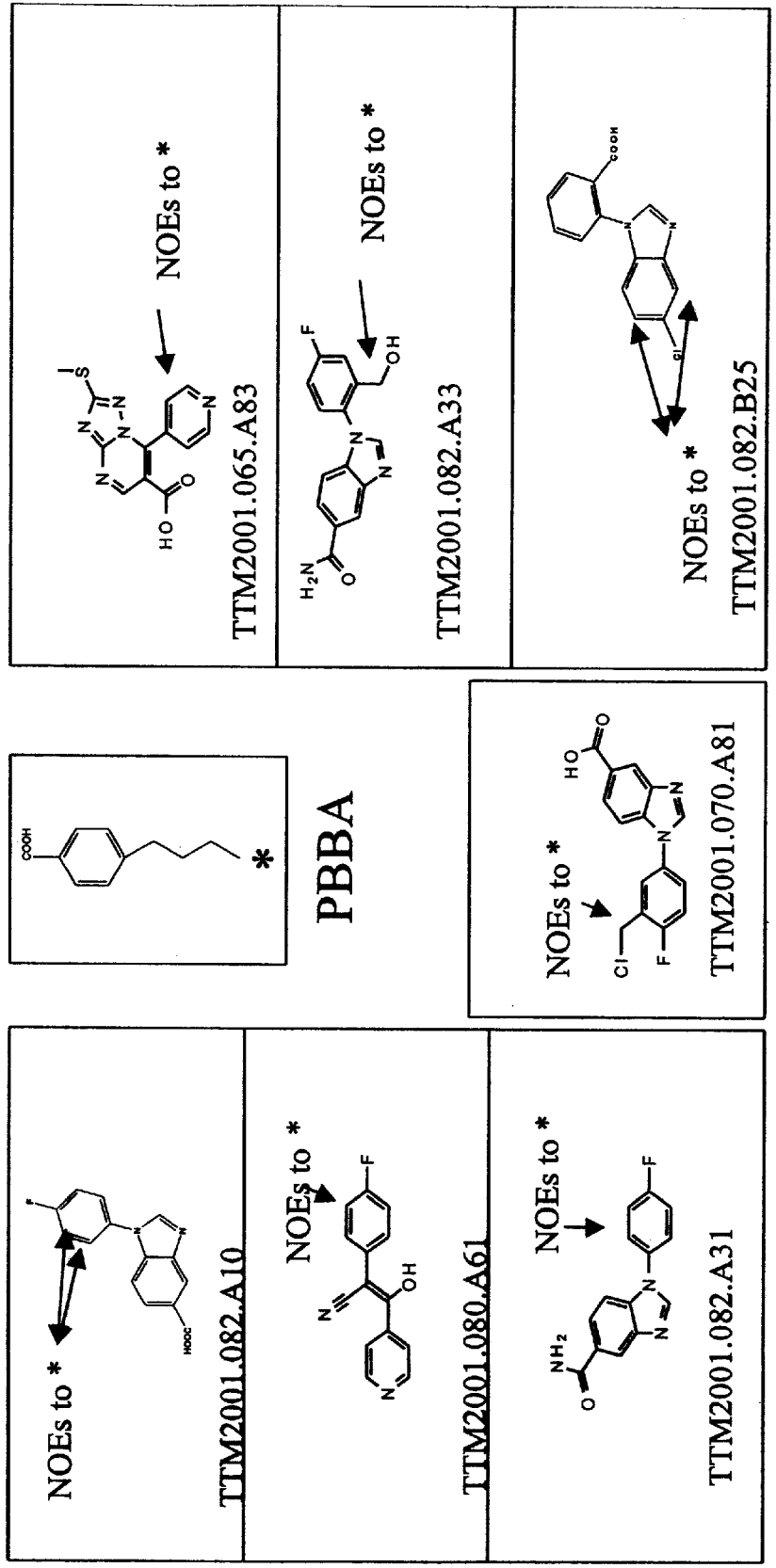
FIG. 2 shows structures for ligands that are proximal to PBBA when bound to p38α MAP kinase, where the PBBA terminal methyl is represented by an asterisk in part b and atoms that have NOE interactions are indicated by arrows.

Potential inhibitors designed to mimic the natural cofactor, as determined by visual inspection of commercially available compounds and assessment of the scientific literature pertaining to kinase medicinal chemistry, were screened against a complex of p38α and PBBA as follows. Samples containing 10 to 30 micromolar concentration of unactivated p38α MAP kinase and 0.1 to 1.0 millimolar concentration of PBBA and 0.1 to 1.0 millimolar concentration of one of the potential inhibitors were obtained. For each sample a 2D [$^1$H, $^1$H] NOESY experiment was performed at 4° C. This process identified 7 molecules that bound proximal to the terminal methyl of PBBA. FIG. 2 shows the structure of PBBA, with the terminal methyl represented by an asterisk and structures of the 7 molecules where arrows indicate the regions of each molecule that contained atoms having NOE interactions with the terminal methyl of PBBA.

Figure 3:
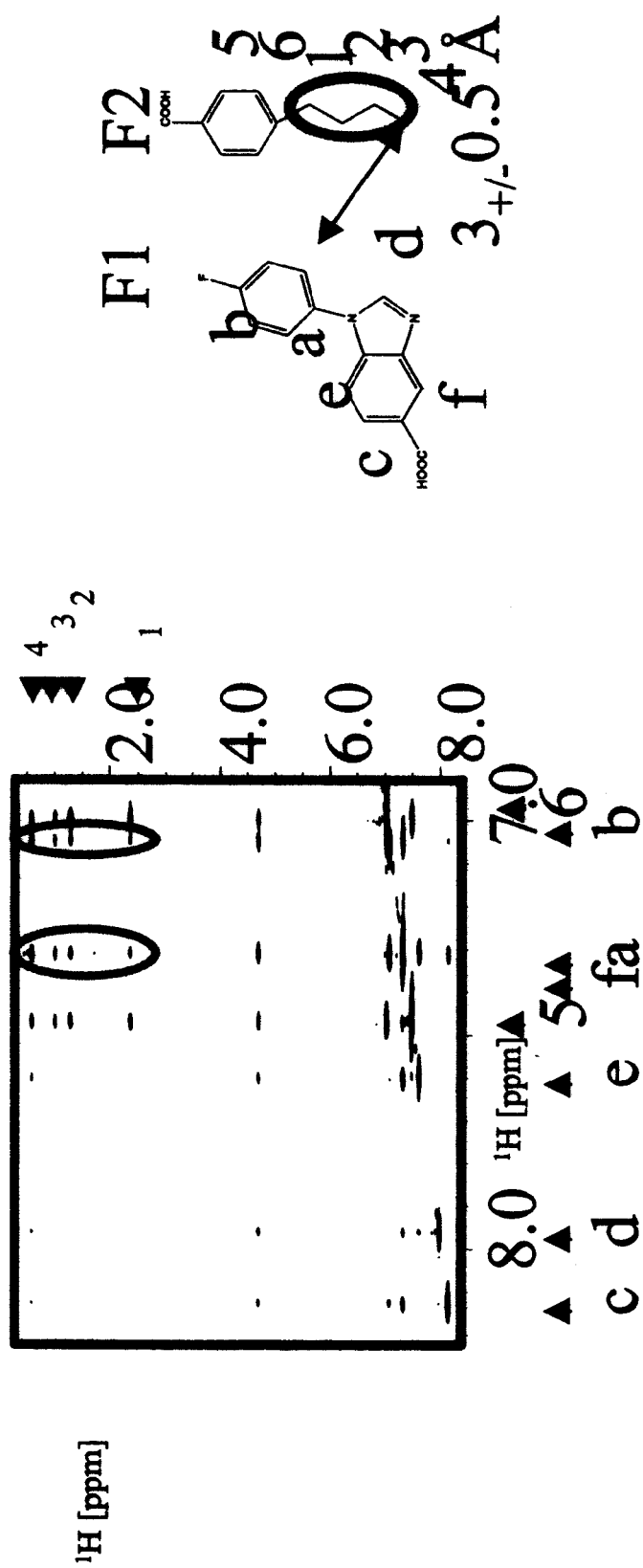
FIG. 3 shows NMR NOESY spectra for PBBA and inhibitor TTM2001.082.B09 when bound to p38α (left panel) and structures for PBBA and inhibitor TTM2001.082.B09 (right panel).

FIG. 3 shows exemplary NMR NOESY data for the ternary complex formed by p38α, PBBA and the TTM2001.082.B09 inhibitor molecule shown in the first panel of FIG. 2a. As shown in FIG. 3, NOE crosspeaks were observed for atoms of the aliphatic moiety of PBBA with atoms of the fluoro-phenyl moiety of the inhibitor TTM2001.082.B09. The crosspeaks indicated that the atoms of the aliphatic moiety of PBBA, identified as atoms 1 to 4 in the right hand panel of FIG. 3, were proximal to the atoms of the fluoro-phenyl moiety of the inhibitor TTM2001.082.B09 that are labeled as atoms a and b in the right hand panel of FIG. 3.

NOE buildup experiments were performed on the sample containing p38α MAP kinase, PBBA and the inhibitor TTM2001.082.B09 and used to determine the distance between atoms 1 to 4 of PBBA and atoms a and b of the inhibitor TTM2001.082.B09. Based on the NOE buildup experiments, the distance between the terminal methyl of PBBA and atom a of the inhibitor TTM2001.082.B09 was determined to be 3±0.5 Å.

The TTM2001.101.A09 bi-ligand compound (shown in FIG. 4) was designed based on the NOE determined distances to contain a moiety similar to the PBBA molecule and a moiety similar to the inhibitor TTM2001.082.B09 joined by a thioether (—CH$_2$—CH$_2$—S—CH$_2$—) linker. The TTM2001.101.A09 bi-ligand compound was synthesized as follows. 4-(6-(Acetylsulfanyl)hexyl) benzoic acid methyl ester (0.985 mmol) was deprotected, removing the thioacetate group, in a biphasic mixture containing potassium carbonate (4.34 mmol) in nitrogen-purged methanol (4 ml), water (2 ml) and tetrahydrofuran (2 ml) that was stirred at room temperature for 1.5 hrs under nitrogen. Esterified TTM2001.101.A09 (1-(4-Fluoro-3-(6-((4-methoxycarbonyl-phenyl)hexylsulfanyl)methyl)phenyl)-1H-benzoimidazole-5-carboxylic acid) was synthesized by then adding 1-(3-Cloromethyl-4-fluor-phenyl)-1H-benzimidazole-5-carboxylic acid (0.820 mmol) to the stirred deprotection mixture. Following work up by removing volatile solvent in vacuo, diluting with water, acidifying with 2N HCl to pH <1, diluting with brine and extracting with ethyl acetate, the esterified TTM2001.101.A09 product was purified with flash chromatography (gradient 95:5 dichloromethane/methanol to 90:10 dichloromethane/methanol). The Ester was removed from the purified product by stirring at room temperature for 15 hours with lithium hydroxide (1.25 mmol) in methanol (1 ml) and water (1 ml), followed by addition of another 1.25 mmol of lithium hydroxide hydroxide and stirring at room temperature for another 24 hours. TTM2001.101.A09 was purified from the mixture by acidification with 2N HCl until pH <2 and collection of the white precipitate by filtration and washing with water and ether.

Figure 4:
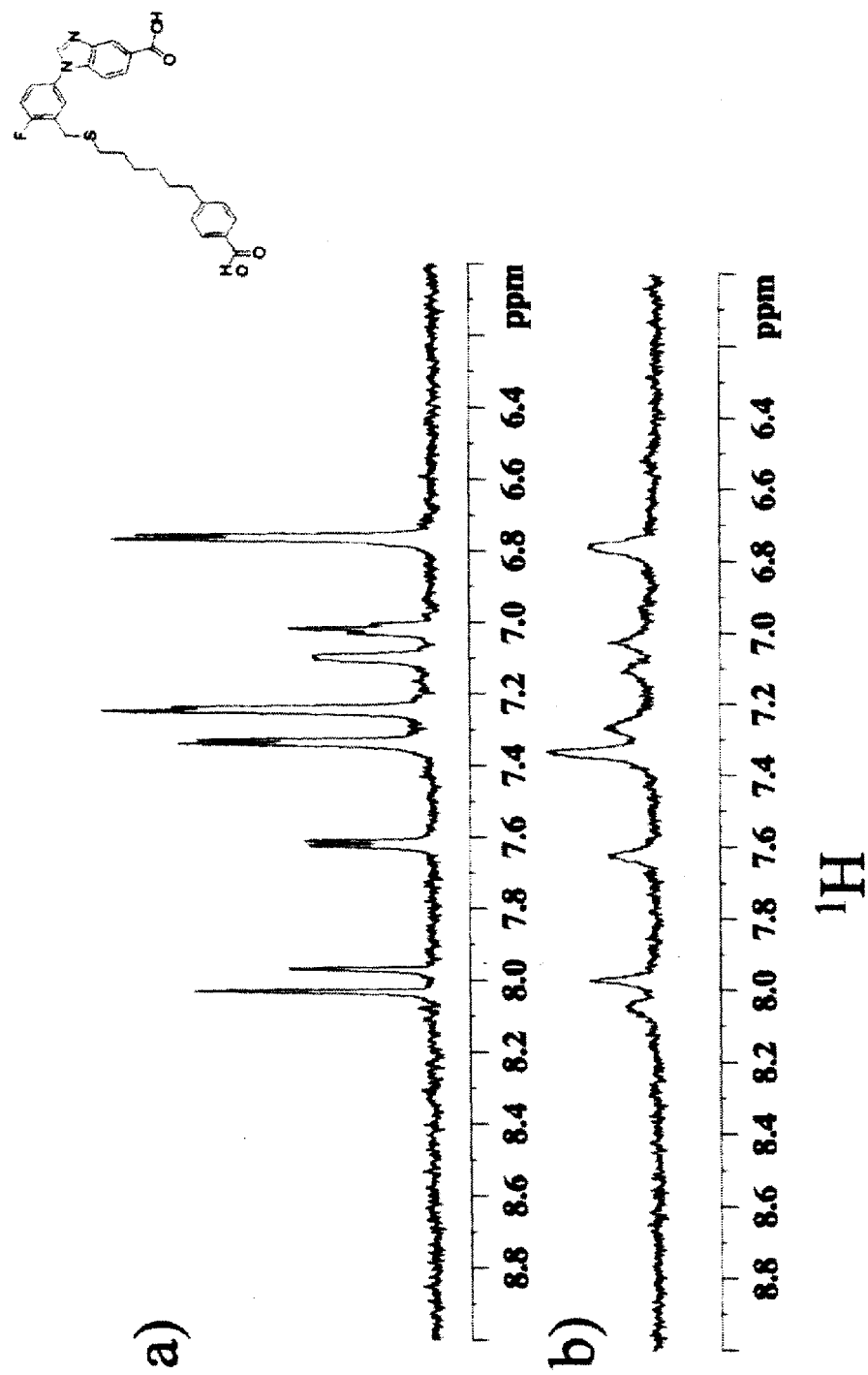
FIG. 4 shows the structure of the TTM2001.101.A09 bi-ligand and $^1$HNMR spectra for the TTM2001.101.A09 bi-ligand in the absence (a) and presence (b) of 10 μM p38α MAP kinase.

The ability of TTM2001.101.A09 to bind to p38α was determined by comparing the degree of line broadening in 1D $^1$H NMR spectra for the compound in the presence of p38α compared to in the absence of p38α. As shown in FIG. 4, significant line-broadening was observed in the 1D $^1$H NMR spectrum of 50 micromolar of TTM2001.101.A09 in the presence of 10 μM of p38α (FIG. 4b) compared to the spectrum obtained for 50 micromolar of TTM2001.101.A09 in the absence of p38α (FIG. 4a), indicative of tight binding between p38α and TTM2001.101.A09.

Figure 5:
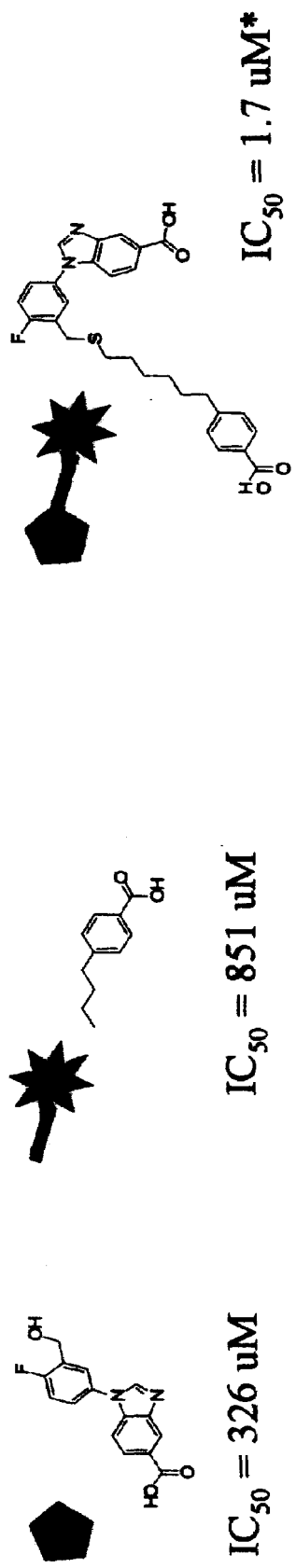
FIG. 5 shows $IC_{50}$ values for inhibition of myelin basic protein phosphorylation by p38α MAP kinase in the presence of inhibitor TTM2001.082.B09, PBBA or TTM2001.101.A09, respectively.

The TTM2001.101.A09 bi-ligand compound and the fragments from which it was constructed were tested as inhibitors of p38α enzymatic activity in an assay measuring phosphorylation of myelin basic protein (MBP) by p38α. The results of the assay are shown in FIG. 5, and indicated that TTM2001.101.A09 bound to p38α with an IC$_{50}$ of 1.7 micromolar, which was greater than 100 fold tighter than either of the starting fragments. Correction of the IC$_{50}$ of TTM2001.101.A09 for high ATP concentration indicated that the K$_d$ for binding between p38α and TTM2001.101.A09 was about 300 nanomolar.

Example II

Combinatorial Matching of Fragments with the MOTIF Library

This example demonstrates the creation of a library of molecules, termed a MOTIF library, having sub-structural features or moieties that are commonly found in marketed drugs or other compounds that have been evaluated in a clinical setting. This example further describes the use of NMR ACE to screen a MOTIF library to obtain a bi-ligand that specifically binds a protein.

Figure 6:
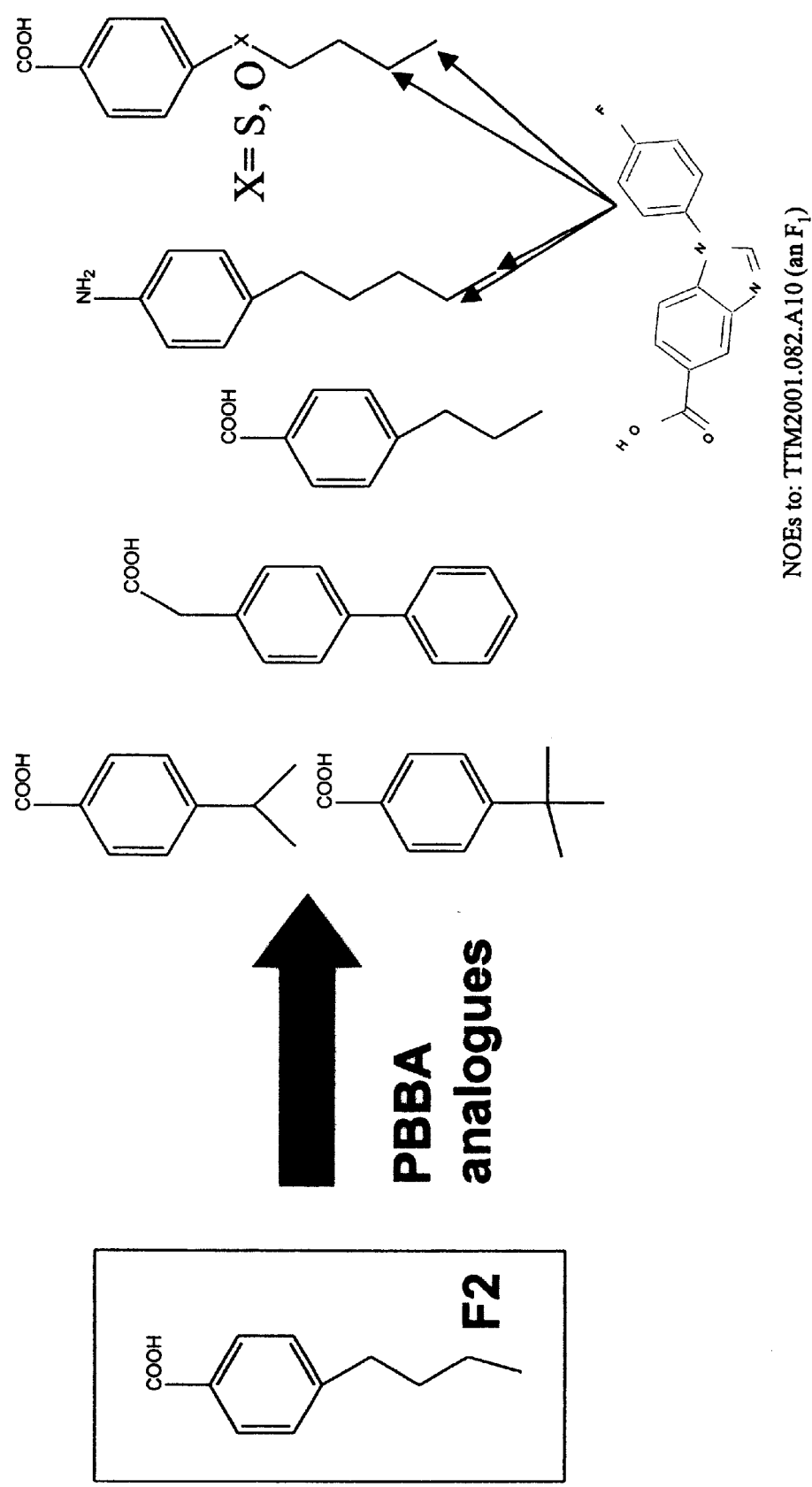
FIG. 6 shows structures for PBBA analogs that bind to p38α MAP kinase. Atoms that have NOE interactions with TTM2001.070.A10 are indicated by arrows.

A number of PBBA related compounds were screened with WaterLOGSY to identify those that bound to p38α. Water- LOGSY screening identified the ligands shown in FIG. 6. Of the compounds shown in FIG. 6, two were identified by cross-saturation experiments (with 10 μM unactivated p38α, 1.5 s to 3.0 s saturation with a train of IBURP pulses) to interact with TTM2001.082.A10 as indicated by the arrows.

A library, referred to as the MOTIF library, containing molecules having sub-structural features or moieties that are commonly found in marketed drugs, as well as other compounds that have been evaluated in a clinical setting was constructed as follows. A database of compounds that are either marketed as drugs or that have undergone clinical trials was created. The database contained over 3500 different chemical entities. The prevalence of particular fragments in the database was analyzed. For example, the diphenyl amine moiety was found in 96 out of 3882 compounds, or 2.5% of the compounds. Moreover, this moiety was found in multiple pharmacological classes. Thus, diphenylamine was identified as a small molecular weight molecule that can be used as part of a screening library for NMR ACE.

Small molecules that contain the diphenyl amine moiety were included in the MOTIF library. Other criteria for determining whether a molecule was to be included in the MOTIF library included a maximum molecular weight of 220 Daltons and chemical inertness under the assay conditions. Based on these criteria a diverse MOTIF library of 160 small drug-like compound fragments was arrayed in multiwell plates for screening.

The MOTIF library members were characterized in terms of solubility and 1D and 2D COSY NMR spectroscopy to obtain proton assignments. The members of the MOTIF library that were found to have favorable characteristics such as solubility and resolved assignable protons were then screened against samples containing a complex of p38α and one of the 6 PBBA-related compounds shown in FIG. 6. The screen was repeated such that each member of the MOTIF library, that was found to have favorable characteristics, was screened against six different samples containing p38α and, respectively, each of the PBBA-related compounds shown in FIG. 6. Samples found to contain ternary complexes were further analyzed by NOE buildup experiments to determine distances between pairs of MOTIF library members and PBBA-related compounds in the ternary complexes. One pair of ligands that bound proximal to each other with p38α was TTM2001.082.A10 and TTE2001.084.47A.

Bi-ligand binding compounds are synthesized to have covalently attached moieties based on the chemical identities of and distances between the pairs of MOTIF library members and PBBA-related compounds that are found to be proximal in the ternary complexes.

Example III

Gene Family Focused Libraries with NMR ACE

This example demonstrates the use of competition experiments and structure analysis combined with NMR ACE to design focused libraries targeted to a particular protein or family of proteins.

Figure 7:
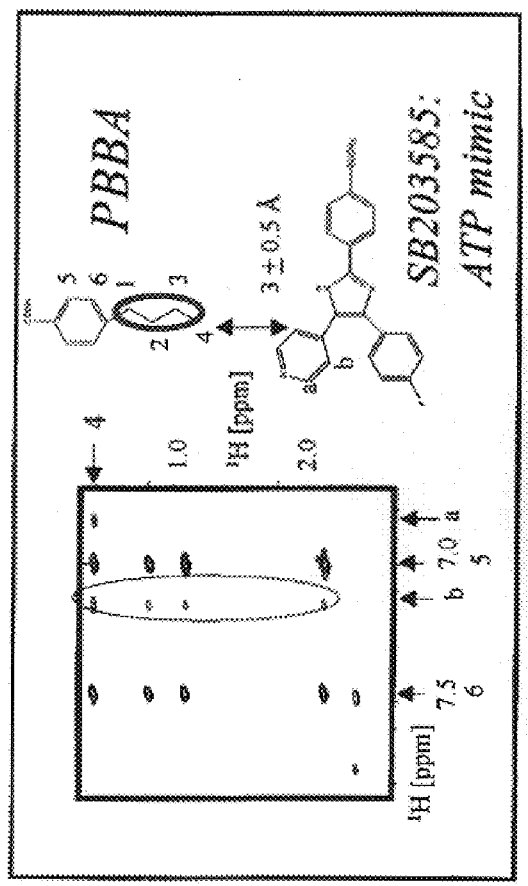
FIG. 7 shows NMR NOESY spectra for PBBA and SB203580 when bound to p38α and structures for PBBA and SB203580 (upper panel) and a crystallographic structure model of the SB203580/p38α complex where the PBBA binding region is indicated by the white oval (lower panel).
Figure 7:
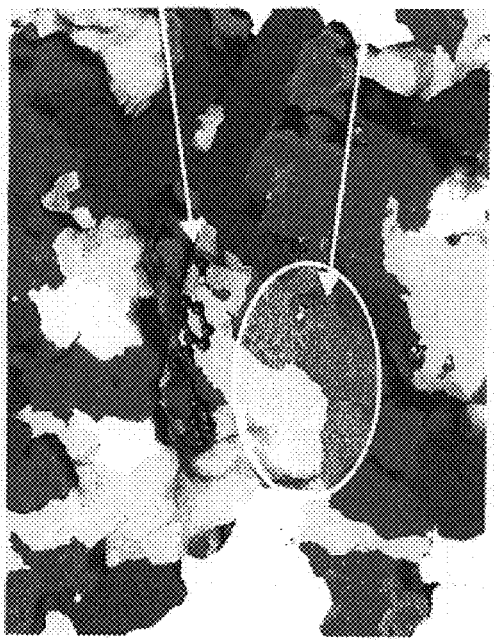

Using the methods described in Example I, PBBA and SB203580 were found to bind to p38α to form a ternary complex where PBBA was proximal to SB203580. As shown in the upper panel FIG. 7, NOE interactions were observed between atom 4 of PBBA and atoms a and b of SB203580. Based on NOE buildup experiments the distance between atom 4 of PBBA and atom b of SB203580 was determined to be 3±0.5 Å. Thus, PBBA bound to p38α at a site that was proximal to the ATP common ligand binding site.

Specificity Pocket

The location where PBBA binds to p38α was predicted as follows. SB203580 is a known inhibitor of p38α that shows competitive binding with ATP in enzymatic assays, indicating that it binds in the ATP site. Binding of SB203580 to the ATP site of p38α has also been observed with a crystal structure of the SB203580/p38α complex shown in the lower panel of FIG. 7 (see Wang et al. *Structure* 6:1117-1128 (1998) and Protein Data Bank entry 1BL6.pdb). Cross-saturation competition studies indicated that SB203580 was not able to displace PBBA. Furthermore, PBBA was not able to displace a fluorescently tagged staurosporine in a fluorescence polarization experiment. Staurosporine is known to bind in the ATP site of p38α. Thus, both NMR and traditional displacement experiments indicated that PBBA did not bind in the ATP site.

A peptide having the sequence IPTTPITTTYFFFKKK (SEQ ID NO:1) is a known phosphorylation substrate for p38α as described, for example, in Chen et al. *Biochemistry* 39:2079-2087 (2000). This peptide could not displace PBBA from p38α in WaterLOGSY competition experiments, indicating that the peptide and PBBA occupied different binding sites on p38α. However, PBBA was shown to inhibit phosphorylation of MBP protein by p38α as described in Example I and shown in FIG. 5. Since the Mbp binding site includes, but extends beyond the peptide binding site, these various competition experiments suggest that PBBA binds in a part of the MBP substrate binding site that extends beyond the peptide binding site. This site is shown in the lower panel of FIG. 7, and is referred to as the SL (specificity ligand) site, since extending a bi-ligand library into this site off of an ATP mimic might provide additional specificity.

Figure 8:
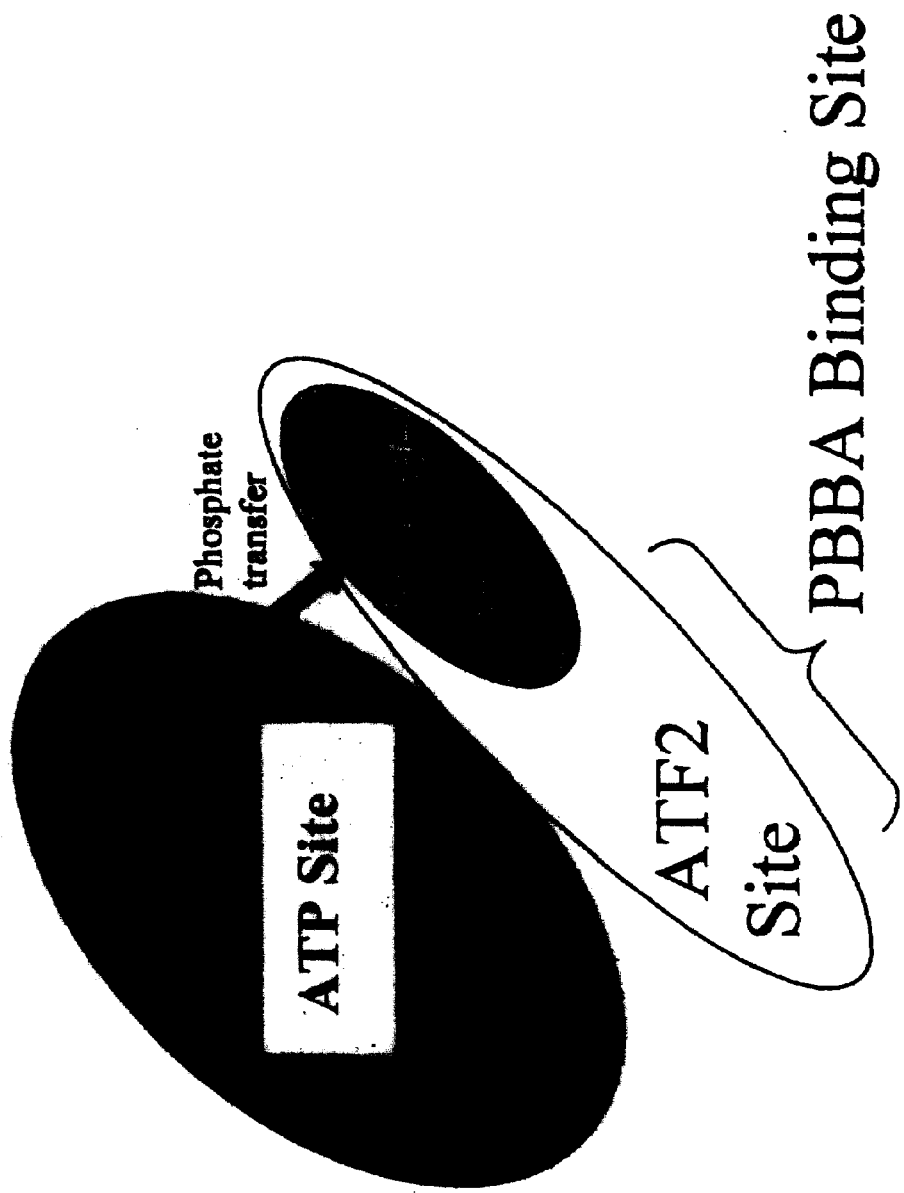
FIG. 8 shows a schematic diagram of the relative locations where ATP (dark circle), myelin basic protein (white circle), peptide (grey circle) and PBBA (area within the white circle and indicated by brackets) bind to p38α MAP kinase.

Based on the distances determined between PBBA and SB203580, the location where SB203580 binds to p38α, and the results of the competitive binding assays described above, the relative locations of the binding regions of p38α for ATP, MBP, the peptide of SEQ ID NO:1 and PBBA were determined. A schematic diagram showing the relative locations of these binding regions is provided in FIG. 8. As shown in FIG. 8, the ATP binding region (dark shaded region) is adjacent to the MBP binding region (white region) and within the MBP region is a region where PBBA binds (indicated by brackets) as well as a region where the peptide (SEQ ID NO:1, lightly shaded region) binds. As shown in FIG. 8, the region of p38α where PBBA binds is separate from the region of p38α where phosphorylation occurs.

Figure 9:
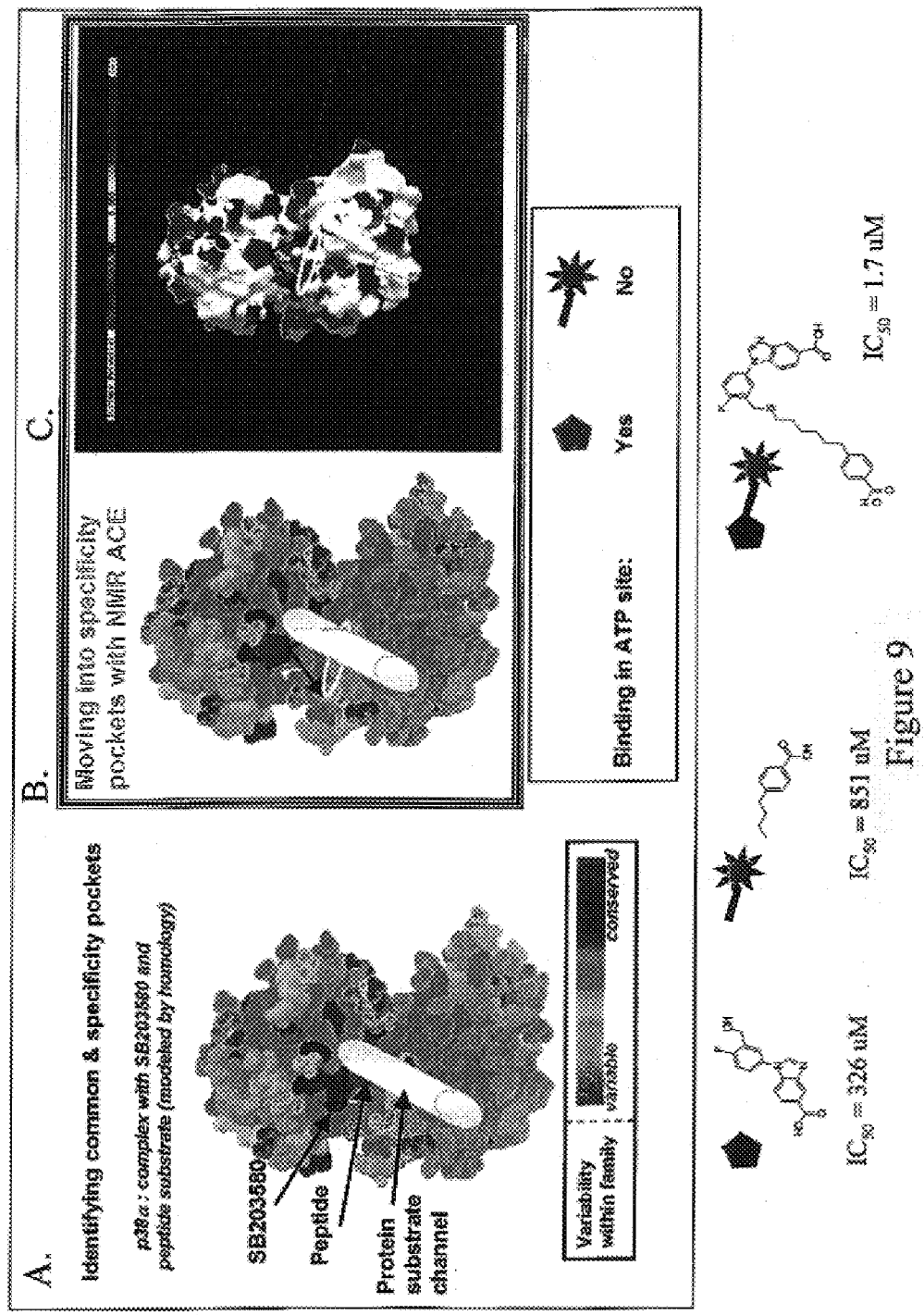
FIG. 9 shows a structure model of p38α derived from Wang et al. *Structure* 6:1117-1128 (1998) in which residues are colored to indicate homology within the family of p38α-like proteins. The pentagon indicates the location of inhibitor SB203580 binding and the white circle indicates the location of PBBA binding, both determined from docking simulations.

The locations of the binding regions of p38α for ATP, Mbp, the peptide of SEQ ID NO:1 and PBBA were further defined based on a structural comparison of p38α-like proteins as follows. FIG. 9A shows a portion of the model of the p38α structure from Wang et al. supra (1998)(Protein Data Bank entry 1BL6.pdb) which includes the regions diagramed in FIG. 8 and where residues are color coded based on the degree of conservation between the residues of the p38α-like proteins. The degree of conservation was determined using PrISM (Yang and Honig *Proteins* 37:66-72 (1999)) and Psi-blast (Altschul et al., *Nucleic Acids Res.* 25:3389-3402 (1997)). Residue conservation scores were obtained from the multiple structure and sequence alignments, which range from highly homologous (blue) to distantly related (red) residues. As shown in FIG. 9, the region of p38α that binds PBBA is variable. Because the region where PBBA binds is variable it is termed a specificity ligand site of p38α. The ATP binding site has a conserved structure and is referred to as a common ligand site of the p38α-like proteins.

The peptide (SEQ ID NO:1) was modeled into the p38α structure based on its location in the PKCα crystal structures described in Nishikawa et al. *J. Biol. Chem.* 272:952-960

(1997); Nair et al. *J. Med. Chem.* 38:4276-4283 (1995); Songyang et al. *Cur. Biol.* 4:973-982 (1994); Songyang et al. *Mol. and Cell. Biol.* 16:6486-6493 (1996). Incorporating residue conservation scores as the starting point, computational docking simulations were performed with small molecules using GOLD and other known methods as described, for example, in Doucet and Weber, "Computer-Aided Drug Design" Academic Press (1996). The simulations showed that molecules, such as PBBA, docked into the specificity region indicated by the circle in FIG. 9B. The location of the SB203580 ATP mimic is represented with a pentagon in FIG. 9 and the relationship between PBBA and SB203580 is indicated with arrows. The arrows span the cone of area that can be occupied by the benzoic acid moiety of PBBA, when constrained to have the terminal methyl proximal to SB203580 according to the NOE of FIG. 7. The electrostatic surface potential map of p38α was calculated using the Grasp algorithm (the Grasp algorithm is described, for example, in Nicholl et al. *Proteins: Strut. Func. and Genet.*, 11:281-296, (1991)).

Design of a Focused Library

Based on the results described above, the region of p38α that binds PBBA is predicted to be a target for binding compounds having specificity for a particular member of this gene sub-family. The proximity of this specificity ligand site to the relatively conserved ATP site indicates that a bi-ligand library can be constructed in which a common ATP or ATP-like moiety is linked to one of a variety of moieties that are similar to PBBA or that bind to the same site as PBBA. A moiety that binds to the same site as PBBA is determined by docking a model of the moiety to the PBBA binding site, by structural comparison to PBBA or by identifying ligands that bind to p38α in an in vitro binding assay.

In order to create a focused library that is specific to p38α and related protein kinases, moieties can be chosen based on specificity for the PBBA binding site of p38α compared to other p38α-like proteins.

Example IV

Identifying Ligand Location with a Ligand-Probe Containing an Antenna Moiety

This example demonstrates the use of a common ligand-probe having an antenna moiety capable of detecting a proximal second ligand. This example further demonstrates discrimination of the relative position and orientation of second ligands using a common ligand-probe having an antenna moiety.

Figure 10:
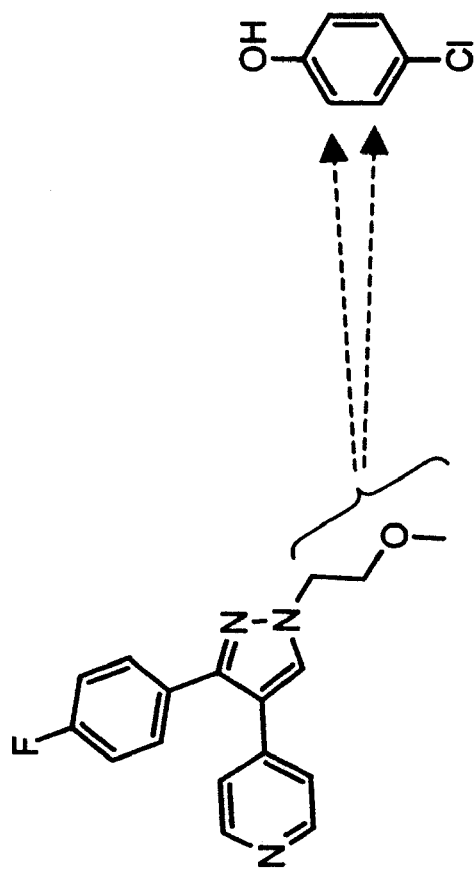
FIG. 10 shows the structures of TTM2002.143.A27 and TTE0020.003.A05 with NOE interactions indicated by arrows.

Ligand-probe TTM2002.143.A27 contains an ATP mimic core moiety covalently attached via an amine linkage to a 3-oxabutyl antenna moiety as shown in FIG. 10. The TTM2002.143.A27 ligand-probe was designed based on the binding orientation and position of the parental common ligand in a 3-dimensional structure of the p38α protein kinase. The antenna moiety was placed such that it can extend from the core structure toward a proximal binding site.

The ether linkage in the antenna moiety allows the terminal methyl group to be relatively isolated from the other protons in the ligand probe, thereby favoring observation of direct NOE transfer from the methyl to a proximal ligand. The ether linkage allows greater differentiation of direct NOE interactions between the methyl and a proximal ligand compared to indirect NOE interactions from a proximal ligand through the core moiety of the ligand probe to the methyl. Isolation of the methyl group due to distance from the other protons allows direct NOE transfer to be selectively observed by obtaining spectra at relatively short mixing times. Furthermore, the absence of vicinal protons minimizes relaxation effects for the methyl protons, thereby providing a stronger signal.

From the MOTIF library, described in Example II, 25 compounds were identified that bound to the p38α protein kinase at sites different from the common ligand. These 25 compounds were screened for proximal binding near the core of the parental common ligand as follows. Samples were obtained containing 100 to 1000 micromolar concentrations of the TTM2002.143.A27 ligand-probe, 10 to 50 micromolar concentrations of activated p38α protein kinase, and one of the 25 compounds at a concentration of 100 to 1000 micromolar. The samples were screened for proximal ligand interactions by ($^1$H, $^1$H) 2D NOESY acquisitions using mixing times of 100-1200 msec at 4° C.

Among the 25 compounds screened, p-chloro-phenol (PCP, TTE0020.003.A05) exhibited NOEs to protons located within the antenna moiety of the TTM2002.143.A27 ligand-probe. As summarized in FIG. 10, for the p38α-TTM2002.143.A27-PCP ternary complex, NOEs were identified between the aromatic hydrogen protons of PCP and the aliphatic protons in the antenna of TTM2002.143.A27. No NOE crosspeaks of significant intensity were observed from PCP to aromatic protons in the core of the parental common ligand in NOESY spectra. Thus, the binding site of PCP appeared to be restricted to a location on the surface of p38α that was within 6.0 Å of the antenna moiety, but at a distance greater than 6.0 Å from the aryl rings in the core moiety of TTM2002.143.A27. Inter-ligand distance between the PCP ligand and antenna moiety are determined based on inspection of the build-up of intensity in NOESY interactions as a function of mixing time ($\tau_m$).

Figure 11:
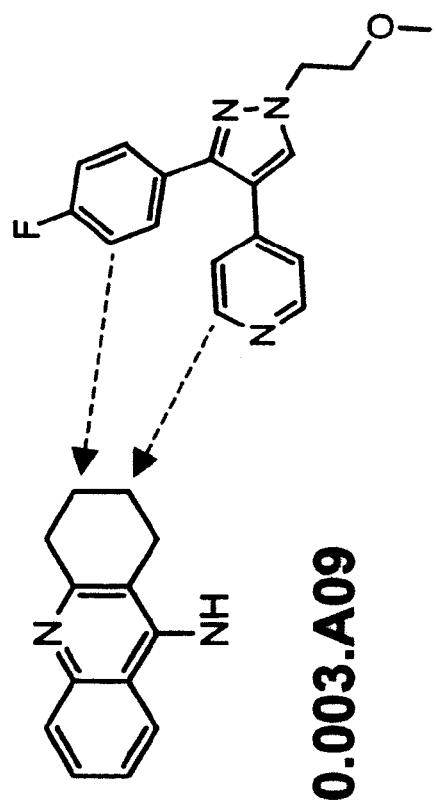
FIG. 11 shows the structures of TTE0020.003.A09 and TTM2002.143.A27 with NOE interactions indicated by arrows.

Also among the 25 compounds screened, the TTE0020.003.A09 ligand was found to bind proximal to the TTM2002.143.A27 ligand-probe. As summarized in FIG. 11, NOE cross peaks were observed between aliphatic protons of the TTE0020.003.A09 second ligand and the core moiety of the ligand probe. However, no significant inter-ligand NOE cross-peaks were observed to the antenna-probe. Thus, the binding site of TTE0020.003.A09 appeared to be at a location of p38α that was within 6.0 Å of the aryl rings in the core moiety of TTM2002.143.A27, but at a distance greater than 6.0 Å from the antenna moiety.

Comparison of the NOEs observed between the ligand-probe and PCP with the NOEs observed between the ligand-probe and TTE0020.003.A09, indicates that addition of the antenna provides information discriminating between the locations of the differing binding sites for second ligands.

Example V

Identification of Proximal Ligands by Selective Cross Saturation of an Antenna Moiety This example demonstrates identification of proximal ligands using selective cross saturation of protons of an antenna moiety attached to a ligand probe.

Ligand-probe TTM2002.143.A27 was obtained as described in Example IV. The protons of the terminal methyl group of the antenna moiety can be selectively saturated compared to other protons of the ligand probe because the methyl is isolated by the adjacent ether group and because the frequency of saturation for the methyl protons is different from that of the aromatic ring protons.

The 25 compounds from the MOTIF library described in Example IV were screened for proximal binding near the ligand-probe as follows. Samples were obtained containing 100 to 1000 micromolar concentrations of the TTM2002.143.A27 ligand-probe, 10 to 50 micromolar concentrations of activated p38α protein kinase, and one of the 25 compounds at a concentration of 100 to 1000 micromolar. Samples were screened for the presence of second ligands binding proximal to the common ligand-probe by ($^1$H) 1 dimensional saturation transfer difference experiments using saturations times of 2 s (frequency selective excitation via a train of 232 6 ms τ pulses with a GAUSS profile at an 80 Hz RF field strength) with solvent suspension using WATER-GATE at 4° C.

Figure 12:
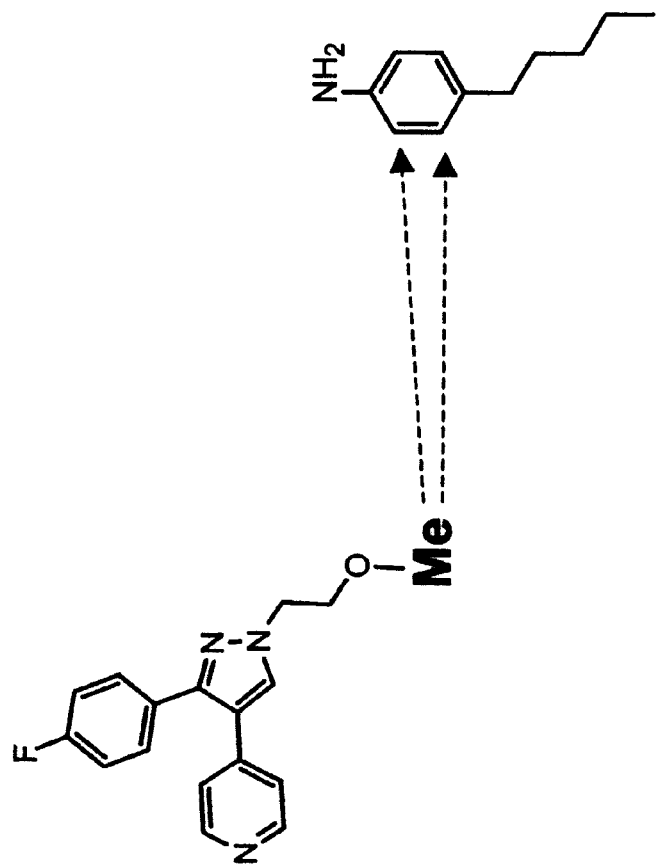
FIG. 12 shows the structures of TTM2002.143.A27 and TTE0020.002.H10 with NOE interactions indicated by arrows.

Among the compounds screened, the aromatic protons of p-pentyl-aniline (PPA) showed a reduction in the intensity on selective saturation of the methyl protons located within the terminus of the antenna-probe (2 s saturation at 3.0 ppm), relative to a control experiment (with off-resonance saturation 5000 Hz up-field). As summarized in FIG. 12 intensity changes were observed for two aromatic protons in a second ligand (TTE0020.003.A09) indicating that they were proximal to the antenna probe when bound to p38α.

These results demonstrate that proximally bound ligands can be identified by observing reduced intensity of resonances for protons in a second ligand that bind close to an antenna moiety for which the proton resonances have been selectively saturated. Such one-dimensional NMR experiments can be performed in minutes, allowing a roughly ten-fold reduction in the screening time per compound compared to 2D NOESY based methods. Such a pre-selection approach can be applied prior to detailed characterization by 2D ($^1$H, $^1$H) NOESY or as an alternative to 2D approaches, to increase screening throughput and reduce instrumentation demands.

Throughout this application various publications, patents and patent applications have been referenced. The disclosures of these publications, patents and patent applications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

What is claimed is:

1. A method for obtaining a binding compound having specificity for a member of an enzyme family, wherein the members of the enzyme family bind a common ligand, comprising the steps of:
   (a) observing competitive binding of the common ligand and a first ligand to a first enzyme;
   (b) observing competitive binding of the common ligand and a first ligand to a second enzyme, wherein the first and second enzymes are members of the enzyme family, thereby determining that the first ligand binds to a common ligand binding site of the first and second enzymes;
   (c) providing a sample comprising the first enzyme, the first ligand and a second ligand;
   (d) providing a sample comprising the second enzyme, the first ligand and the second ligand;
   (e) determining the degree of magnetization transfer between the first ligand and the second ligand for the samples of parts (c) and (d);
   (f) comparing the degree of magnetization transfer between the first ligand and the second ligand for the samples of parts (c) and (d), whereby comparing the degree of magnetization transfer identifies a second ligand that selectively binds to the first or second enzyme; and
   (g) generating a binding compound by linking the first ligand, or a binding fragment thereof, to the second ligand or a binding fragment thereof via a linker, said linker joining proximal portions of said first and said second ligands;
   thereby obtaining a binding compound having specificity for the first enzyme, wherein said second ligand selectively binds to the first enzyme, or having specificity for the second enzyme, wherein said second ligand selectively binds to the second enzyme.

2. The method of claim 1, wherein the enzymes contain a natural abundance of isotopes for carbon or nitrogen.

3. The method of claim 1, wherein the enzymes are present in the samples at a concentration less than 200 micromolar.

4. The method of claim 1 wherein the enzymes have a monomeric molecular weight greater than 30 kDa.

5. The method of claim 1, wherein the enzymes are deuterium labeled.

6. The method of claim 1, wherein the binding compound has at least 2 fold higher affinity for the first enzyme compared to the second enzyme.

7. The method of claim 1, wherein the degree of magnetization transfer is determined by measuring cross-saturation.

8. The method of claim 7, wherein the cross-saturation is measured using water ligand observed via gradient spectroscopy (WaterLOGSY).

9. The method of claim 1, wherein step (f) further comprises measuring magnetization transfer at a temperature below 10° C.

10. The method of claim 9, wherein measuring magnetization transfer comprises obtaining a 2D ($^1$H, $^1$H) Nuclear Overhauser Effect Spectroscopy (NOESY) spectrum.

11. The method of claim 1, wherein step (f) further comprises identifying an atom of the first ligand that is proximal to an atom of the second ligand.

12. The method of claim 11, further comprising determining the distance between the atom of the first ligand that is proximal to the atom of the second ligand.

13. The method of claim 12, wherein a linker connects the first ligand, or fragment thereof, and the second ligand such that the first ligand, or fragment thereof can be separated from the second ligand by the distance separating them in the bound complex.

14. The method of claim 12, wherein the first ligand, or fragment thereof, and the second ligand, or fragment thereof, are linked at the positions of the proximal atoms of the first and second ligands.

15. The method of claim 1, wherein the first ligand comprises a ligand-probe having an antenna moiety.

16. The method of claim 15, wherein step (e) comprises comparing the degree of magnetization transfer between the antenna moiety of the ligand-probe and the second ligand for the samples of parts (b) and (c).

17. The method of claim 15, wherein the ligand-probe comprises a common ligand attached to the antenna moiety.

* * * * *

UNITED STATES PATENT AND TRADEMARK OFFICE
CERTIFICATE OF CORRECTION

PATENT NO. : 7,653,490 B2  Page 1 of 1
APPLICATION NO. : 10/172485
DATED : January 26, 2010
INVENTOR(S) : Sem et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 405 days.

Signed and Sealed this

Twenty-third Day of November, 2010

David J. Kappos
*Director of the United States Patent and Trademark Office*